US012685872B2

(12) United States Patent
Rosenbloom et al.

(10) Patent No.: US 12,685,872 B2
(45) Date of Patent: Jul. 21, 2026

(54) METHOD AND DEVICE FOR MEDICALLY TREATING NASAL AND THROAT CONDITIONS WITH COLD PLASMA

(71) Applicant: Ionos Medical Inc., San Antonio, TX (US)

(72) Inventors: Jeffrey S. Rosenbloom, San Antonio, TX (US); Gregory Fridman, Philadelphia, PA (US)

(73) Assignee: Ionos Medical Inc., San Antonio, TX (US)

( * ) Notice: Subject to any disclaimer, the term of this patent is extended or adjusted under 35 U.S.C. 154(b) by 6 days.

(21) Appl. No.: 18/443,494

(22) Filed: Feb. 16, 2024

(65) Prior Publication Data

US 2024/0278030 A1 Aug. 22, 2024

Related U.S. Application Data

(60) Provisional application No. 63/485,370, filed on Feb. 16, 2023.

(51) Int. Cl.
| | |
|---|---|
| *A61N 1/44* | (2006.01) |
| *A61L 2/14* | (2006.01) |
| *A61B 18/00* | (2006.01) |

(52) U.S. Cl.
CPC .................. *A61N 1/44* (2013.01); *A61L 2/14* (2013.01); *A61B 2018/00291* (2013.01); *A61B 2018/00327* (2013.01); *A61B 2018/00583* (2013.01)

(58) Field of Classification Search
CPC ............ A61N 1/44; A61B 2018/00291; A61B 2018/00327; A61B 2018/00583; A61B 18/042
See application file for complete search history.

(56) References Cited

U.S. PATENT DOCUMENTS

| | | | | |
|---|---|---|---|---|
| 2005/0234439 A1* | 10/2005 | Underwood | ....... | A61B 18/1485 |
| | | | | 606/41 |
| 2008/0287893 A1* | 11/2008 | Ineson | ................... | A61B 18/00 |
| | | | | 604/319 |

(Continued)

FOREIGN PATENT DOCUMENTS

GB 2607040 A 11/2022

OTHER PUBLICATIONS

"Gallium," Utoledo.edu. [Online]. Available: https://www.utoledo.edu/nsm/ic/elements/gallium.html. [Accessed: Nov. 21, 2025]. (Year: 2025).*

(Continued)

*Primary Examiner* — Joanne M Rodden
*Assistant Examiner* — Dana Stumpfoll
(74) *Attorney, Agent, or Firm* — Vos-IP, LLC

(57) ABSTRACT

A medical device for providing nonthermal plasma treatment to a patient by generating sufficient nonthermal plasma in the presence of the flow of an oxygen-free gas mixture that can quickly and safely treat infection or promote wound healing in the desired region wherein the device is flexible and easy to maneuver in difficult to access regions such as the nose, paranasal sinuses, throat, esophagus, and ears of a patient and wherein the device comprises an integrated vacuum/suction to capture reactive species that are generated by plasma to prevent the patient from inhaling harmful byproducts.

14 Claims, 10 Drawing Sheets

(56)                References Cited

U.S. PATENT DOCUMENTS

| | | | |
|---|---|---|---|
| 2009/0054896 A1* | 2/2009 | Fridman | A61B 18/042 |
| | | | 606/49 |
| 2010/0145253 A1 | 6/2010 | Gutsol et al. | |
| 2011/0245759 A1* | 10/2011 | McCaney | A61P 31/12 |
| | | | 604/24 |
| 2012/0100524 A1 | 4/2012 | Fridman et al. | |
| 2012/0107896 A1* | 5/2012 | Wandke | H05H 1/2441 |
| | | | 435/173.6 |
| 2012/0156091 A1 | 6/2012 | Fridman et al. | |
| 2012/0253265 A1 | 10/2012 | Fridman et al. | |
| 2012/0296265 A1 | 11/2012 | Dobrynin et al. | |
| 2013/0053762 A1* | 2/2013 | Rontal | A61B 1/015 |
| | | | 604/24 |
| 2013/0261536 A1* | 10/2013 | Sartor | A61B 18/042 |
| | | | 604/23 |
| 2013/0310731 A1 | 11/2013 | Gutsol et al. | |
| 2013/0330229 A1 | 12/2013 | Fridman et al. | |
| 2014/0199756 A1 | 7/2014 | Ish-Yamini Tomer et al. | |
| 2014/0311891 A1 | 10/2014 | Fridman et al. | |
| 2015/0038790 A1* | 2/2015 | Rontal | A61B 1/0051 |
| | | | 604/20 |
| 2016/0121134 A1* | 5/2016 | Kalghatgi | A61N 1/44 |
| | | | 604/23 |
| 2016/0353978 A1* | 12/2016 | Miller | A61B 1/00096 |
| 2016/0361558 A1* | 12/2016 | Jacofsky | A61N 1/44 |
| 2017/0112871 A1* | 4/2017 | Nelson | A61P 9/10 |
| 2017/0202218 A1 | 7/2017 | Fridman et al. | |
| 2017/0296836 A1 | 10/2017 | Dobrynin et al. | |
| 2018/0103991 A1* | 4/2018 | Linhart | A61B 18/1477 |
| 2021/0260395 A1 | 8/2021 | Friedman et al. | |
| 2021/0282831 A1 | 9/2021 | Friedman et al. | |
| 2021/0299461 A1 | 9/2021 | Guy | |
| 2022/0287769 A1 | 9/2022 | Knecht et al. | |
| 2023/0067303 A1* | 3/2023 | Hancock | A61B 18/042 |
| 2023/0126911 A1* | 4/2023 | Uchitel | H05H 1/01 |
| | | | 604/20 |
| 2023/0371998 A1 | 11/2023 | Friedman et al. | |

OTHER PUBLICATIONS

International Search Report issued in International Application No. PCT/US2024/016068 dated Jun. 28, 2024.

Ahmad, et al., "At Low Temperature Plasma Preoperative and Postoperative of Chronic Tonsillitis Tonsillectomy", Saudi Journal of Medical and Pharmaceutical Sciences, vol. 9, No. 12, Dec. 21, 2023, 850-856.

Bhattacharyya, et al., "Economic Benefit of Tonsillectomy in Adults With Chronic Tonsillitis", Annals of Otology, Rhinology & Laryngology, vol. 111, No. 11, Nov. 1, 2002, 983-988.

Chan, et al., "Randomized, Controlled, Multisite Study of Intracapsular Tonsillectomy Using Low-Temperature Plasma Excision", Archives of Otorhinolaryngology—Head & Neck Surgery, vol. 130, No. 11, Nov. 1, 2004, 1303-1307.

Kaygusuz, et al., "Free Radicals and Scavenging Enzymes in Chronic Tonsillitis", Otolaryngology—Head and Neck Surgery, vol. 129, No. 3, Nov. 21, 2016, 265-268.

Manee, et al., "Chronic Rhinitis and Chronic Tonsillitis of Staphylococcal Genesis in Rabbits as Laboratory Animal Model for Experimental Research", Current Issues in Pharmacy and Medical Sciences, vol. 31, No. 3, Oct. 29, 2018, 140-143.

Sedgwick, et al., "Intracapsular Tonsillectomy Using Plasma Ablation Versus Total Tonsillectomy: A Systematic Literature Review and Meta-Analysis", OTO Open, vol. 7, No. 1, art. 22, Feb. 17, 2023, 1-13.

Tang, et al., "Effectiveness of Low-Temperature Plasma Tonsillectomy for Chronic Tonsillitis. A Protocol of Systematic Review and Meta-Analysis", Annali Italiani di Chirurgia, vol. 93, No. 3, May 1, 2022, 280-285.

Yu, "Effect of a Low Temperature Plasma Knife on the Treatment of Chronic Tonsillitis and Its Effect on T Lymphocyte Subsets", American Journal of Translational Research, vol. 13, No. 4, Apr. 15, 2021, 2447-2455.

* cited by examiner

Ozone Concentration

FIGURE 3B

Ozone Concentration (without Air Data)

Gas Composition $N_2$:NO 0.10

Temperature

FIGURE 7A
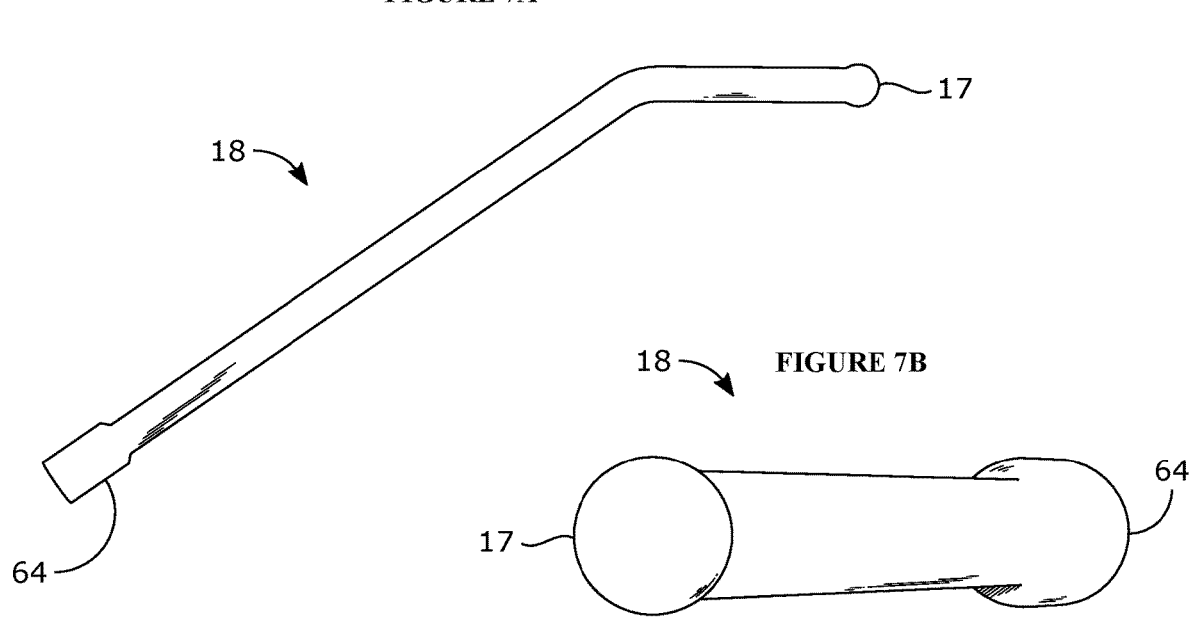
FIGURE 7B
FIGURE 8A
FIGURE 8B
FIGURE 8C
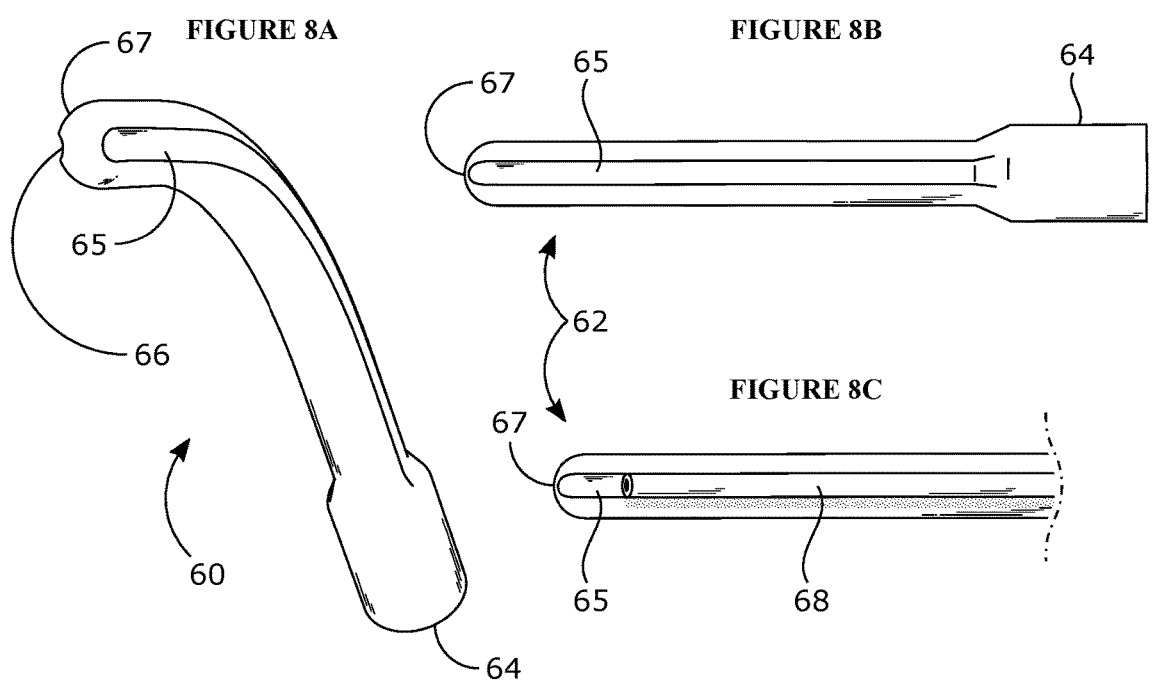

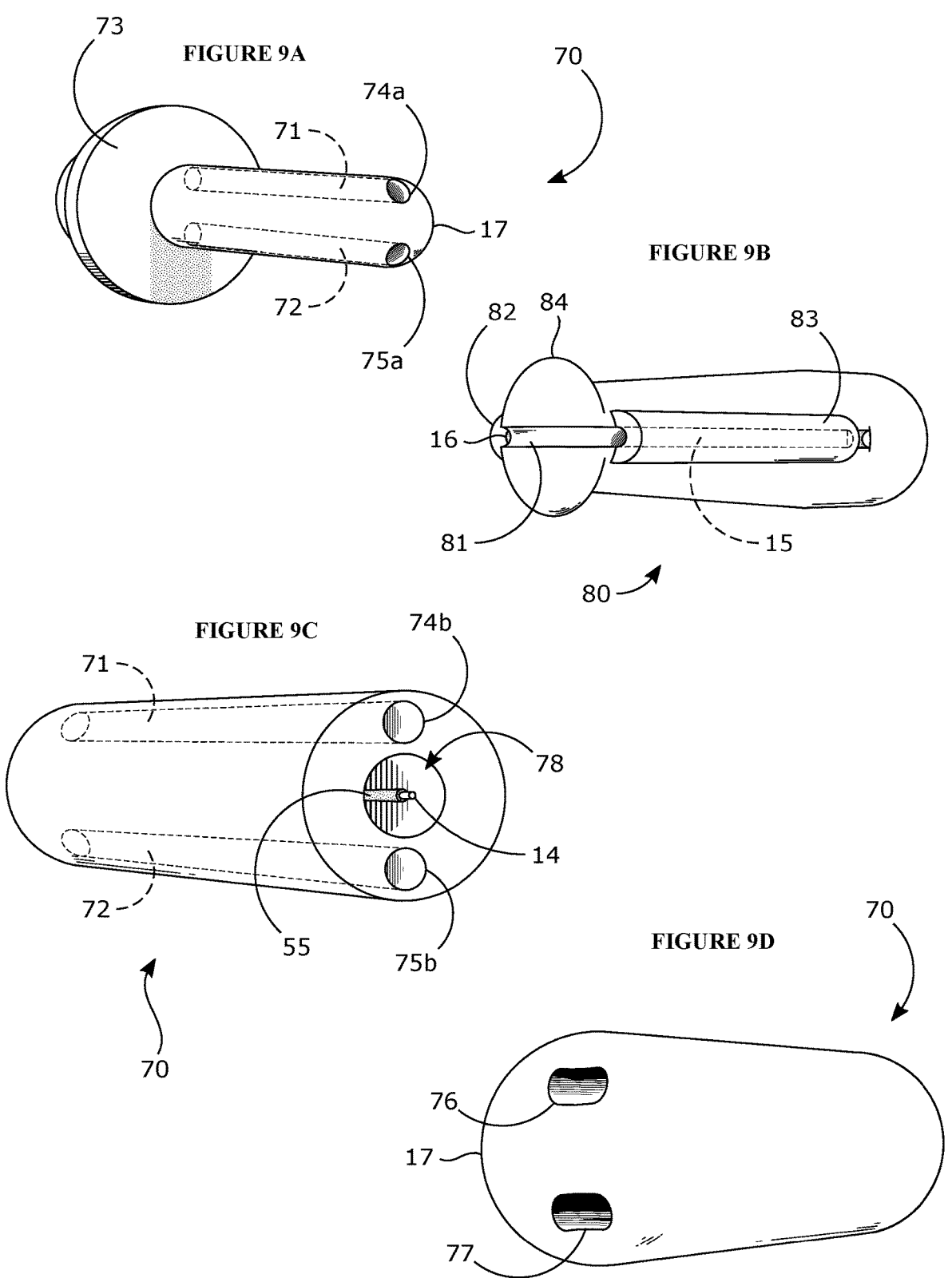

METHOD AND DEVICE FOR MEDICALLY TREATING NASAL AND THROAT CONDITIONS WITH COLD PLASMA

CROSS-REFERENCE TO RELATED APPLICATIONS

This application claims the benefit of U.S. Provisional Application No. 63/485,370 filed on Feb. 16, 2023, with the United States Patent and Trademark Office, the contents of which are incorporated herein by reference in their entirety.

FIELD OF THE INVENTION

The present invention relates generally to a cold plasma medical treatment for ailments or conditions and specifically to treatment of the paranasal sinuses, nose, esophagus, mouth, and ears of a human patient.

BACKGROUND OF THE INVENTION

Some of the most common health problems people experience result from issues that have developed in the nose, throat, and ears of the patient. Tonsillitis alone accounts for an estimated 2% of all hospital visits and about 7.5% of people experience sore throat in any three-month period. Children in particular are susceptible to viral and bacterial infections that develop in the ear, nose, or throat. Many patients' symptoms for throat infections are easily treated with little inconvenience and can be resolved in about a week naturally or with antibiotics. However, some patients experience reoccurring or chronic symptoms that require specialized treatment from an otolaryngologist. Such existing treatments for chronic or reoccurring tonsilitis include a costly tonsillectomy or the surgical removal of the tonsils.

Similarly, a common reason to seek a medical professional's assistance involves issues with a patient's nasal cavity. Pain, discomfort, and difficulty breathing resulting from infection or abnormalities in the nasal cavity affect a large portion of the population and can range from a mild annoyance to a severe disruption in that individual's lifestyle. In such instances costly medical procedures may be required to resolve those nasal issues.

The direct cost of managing acute and chronic sinusitis conservatively exceeds $11 billion per year. The indirect costs with lost days off work and school are heartbreaking. It is estimated that 6% to 12% of patients in the Western world have chronic sinusitis.

Currently, there is development in the medical applications of low temperature nonthermal plasma or "cold plasma" with surprisingly effective results. Plasma is an ionized gas that generates ions, chemically reactive atoms and molecules, and UV-photons. These plasma generated species have been found to be useful for several biomedical applications.

There is a need for an effective and safe treatment for medical issues in the nose, mouth, throat, esophagus, and ears of patients that is less invasive and more convenient than surgery or antibiotic use. As detailed herein, Applicant has advantageously discovered that cold plasma may be effectively utilized for treatment of multiple medical ailments within the ear, nose, esophagus, and throat. Importantly, because of the sensitivity of these tissues, and the proximity to the lungs, Applicant has identified improvements to cold plasma treatment, new methods of treatment, and new devices suitable to reduce or virtually eliminate ozone presence created by the cold plasma by generating cold plasma in the presence of a nonoxygen gas. Furthermore, the nonoxygen gases unexpectedly increased efficacy of the cold plasma treatment. Accordingly, Applicant details herein such devices, and methods of treatment suitable for replacement of conventional antibiotic use or surgery as is often required for treatment of certain ear, nose, esophagus and throat infections and disease.

SUMMARY OF THE INVENTION

Disclosed embodiments are enabled to provide a device and method for medically treating throat, nose, esophagus, and ear of a human subject with the use of cold plasma. By utilizing plasma, efficacy can be achieved without burning or excessively irritating the tissue, a number of medical treatments can be achieved. These treatments include, but are not limited to, the sterilization or removal of biofilm, reduction of enlarged structures, destruction, or inactivation of microorganisms such as bacteria, viruses, fungi, and other pathogenic materials, as well as selectively damaging tissue, or to promote healing of tissue. An integrated or adjacent vacuum is utilized to capture any excess ozone particles that are generated that can cause harm to the patient.

A first objective is to provide safe and effective treatment of a variety ailments of the throat including viral, bacterial, and other microorganism infections such as chronic tonsillitis of a subject. Cold plasma treatment effectively removes biofilm from the tonsils, forgoing the need for a tonsillectomy.

A second objective is to treat a variety of other medical conditions in the throat including, but not limited to, Barrett's esophagus and halitosis.

Another objective is applying a treatment to the nose or nasal cavity to remedy the underlying cause for medical conditions including rhinitis (chronic, allergic, and vasomotor). Cold plasma treatment can be an efficient way to treat a number of nasal cavity related issues, for example, enlarged inferior turbinates and nasal swell bodies can be reduced utilizing cold plasma treatment.

A further objective is to provide treatment to the ear canal to treat conditions such as ceruminosis or the excessive secretion of "ear wax." Cold plasma can be used to selectively injure the cerumen gland and peripheral nerves to cease excessive ear wax secretion.

In a preferred embodiment, a cold plasma device comprising: a probe (18), said probe (18) comprising a conductor wire (14) extending from a proximal end to a distal end and having a tip (17) at said distal end; a first passage having a first opening adjacent to the tip (17) and a second passage having a second opening adjacent to the tip (17); and a power source generating 10,000-45,000 V at a pulse of 0.1 us to 1 s in duration applied at 100 Hz to 10,000 Hz.

In a further embodiment, the cold plasma device wherein the power source most preferably generates 17,000-37,000 V pulses of 1-5 us in duration applied at 1,000 Hz.

In a further embodiment, the cold plasma device wherein the conductor wire comprises an insulating material along a length of the probe from the proximal end to the distal end with a portion of noninsulated material at each end of the conductor wire.

In a further embodiment, the cold plasma device wherein the probe is connected to a pressurized gas and a wiring harness, said wiring harness connected to a power source.

In a further embodiment, the cold plasma device wherein a pressurized gas is configured to flow into the first passage.

In a further embodiment, the cold plasma device defined to provide suction from the second opening adjacent to the tip and through the second passage.

In a further embodiment, the cold plasma device wherein the conductor wire is surrounded by an epoxy along a length of the probe from the proximal end to the distal end.

In a further embodiment, the cold plasma device wherein the tip comprises a conductive metal or metal alloy.

In a further embodiment, the cold plasma device wherein the tip comprises gallium or a gallium alloy.

In a further embodiment, the cold plasma device wherein the first passage and the second passage are attached to an outside portion of the probe or a recess within the probe or are comprised within the probe.

In a further embodiment, the cold plasma device wherein the first passage is provided with nitrogen gas.

In a further embodiment, the cold plasma device wherein the first passage is provided with a mixture of nitrogen gas and nitric oxide.

In a further embodiment, the cold plasma device wherein the first passage is provided with a mixture of nitrogen gas and nitric oxide at a concentration of the nitric oxide of 5,000 ppm and a flow rate of between 0.01 standard liters per minute (SLPM) and 0.15 SLPM.

In a further embodiment, the cold plasma device comprising: a suction of between 0.1 SLPM and 10 SLPM of flow within the second passage; and/or a flow of nitrogen gas into the first passage; and/or a flow of a combination of nitrogen gas and nitric oxide, said nitric oxide at between 1,000 ppm and 10,000 ppm, having a standard liter per minute flow of 0.01 SLPM to 0.15 SLPM.

In a preferred embodiment, use of the cold plasma device for use in treatment of tonsilitis and/or tonsil stones and/or sinusitis and/or nasal infection and/or Barrett's esophagus and/or a combination thereof.

In a preferred embodiment, a method of treatment of tonsillitis comprising administering to a patient in need thereof an effective amount of cold plasma, said cold plasma administered by applying a quantity of cold plasma from a probe from a cold plasma device.

In a further embodiment, the method of treatment wherein the cold plasma is administered by providing a flow of nitrogen gas to a tip of the probe.

In a further embodiment, the method of treatment wherein the cold plasma is administered by providing a suction of air from an opening in a passage adjacent to a tip of the probe.

In a further embodiment, the method of treatment wherein the cold plasma is generated from a probe (18), said probe (18) comprising: a conductor wire (14) extending from a proximal end to a distal end and having a tip (17) at said distal end; a first passage having a first opening adjacent to the tip (17) and a second passage having a second opening adjacent to the tip (17); and a power source generating 10,000-45,000 V at a pulse of 0.1 μs to 1 s in duration applied at 100 Hz to 10,000 Hz.

In a further embodiment, the method of treatment wherein power is provided to the probe at between 17,000-37,000 V having pulses of 1-5 μs in duration applied at 1,000 Hz.

In a further embodiment, the method of treatment wherein the conductor wire comprises an insulating material along a length of the probe from the proximal end to the distal end with a portion of noninsulated material at each end of the conductor wire.

In a further embodiment, the method of treatment wherein the probe is connected to a pressurized gas and a wiring harness, said wiring harness connected to a power source.

In a further embodiment, the method of treatment wherein a pressurized gas is configured to flow into the first passage.

In a further embodiment, the method of treatment defined to provide suction from the second opening adjacent to the tip and through the second passage.

In a further embodiment, the method of treatment wherein the conductor wire is surrounded by an epoxy along a length of the probe from the proximal end to the distal end.

In a further embodiment, the method of treatment wherein the tip comprises a conductive metal or metal alloy.

In a further embodiment, the method of treatment wherein the tip comprises gallium or a gallium alloy.

In a further embodiment, the method of treatment wherein the first passage and the second passage are attached to an outside portion of the probe or a recess within the probe or are comprised within the probe.

In a further embodiment, the method of treatment wherein the first passage is provided with nitrogen gas.

In a further embodiment, the method of treatment wherein the first passage is provided with a mixture of nitrogen gas and nitric oxide.

In a further embodiment, the method of treatment wherein the first passage is provided with a mixture of nitrogen gas and nitric oxide at a concentration of the nitric oxide at 5,000 ppm and a flow rate of between 0.01 SLPM and 0.15 SLPM.

In a further embodiment, the method of treatment comprising: a suction of between 0.1 SLPM and 10 SLPM within the second passage; and/or a flow of nitrogen gas into the first passage; and/or a flow of a combination of nitrogen gas and nitric oxide, said nitric oxide at between 1,000 ppm and 10,000 ppm, having a standard liter per minute flow of 0.01 SLPM to 0.15 SLPM.

In a preferred embodiment, a method of treatment of sinusitis comprising administering to a patient in need thereof an effective amount of cold plasma, said cold plasma administered by applying a quantity of cold plasma from a probe from a cold plasma device.

In a preferred embodiment, a method of treatment of a nasal infection comprising administering to a patient in need thereof an effective amount of cold plasma, said cold plasma administered by applying a quantity of cold plasma from a probe from a cold plasma device.

In a preferred embodiment, a method of treatment of tonsil stones comprising administering to a patient in need thereof an effective amount of cold plasma, said cold plasma administered by applying a quantity of cold plasma from a probe from a cold plasma device.

In a further embodiment, the method of treatment wherein the cold plasma is administered by providing a flow of nitrogen gas to a tip of the probe.

In a further embodiment, the method of treatment wherein the cold plasma is administered by providing a suction of air from an opening in a passage adjacent to a tip of the probe.

In a further embodiment, the method of treatment wherein the cold plasma is generated from a probe (18), said probe (18) comprising: a conductor wire (14) extending from a proximal end to a distal end and having a tip (17) at said distal end; a first passage having a first opening adjacent to the tip (17) and a second passage having a second opening adjacent to the tip (17); and a power source generating 10,000-45,000 V at a pulse of 0.1 μs to 1 s in duration applied at 100 Hz to 10,000 Hz.

In a further embodiment, the method of treatment wherein power is provided to the probe at between 17,000-37,000 V having pulses of 1-5 μs in duration applied at 1,000 Hz.

In a further embodiment, the method of treatment wherein the conductor wire comprises an insulating material along a length of the probe from the proximal end to the distal end with a portion of noninsulated material at each end of the conductor wire.

In a further embodiment, the method of treatment wherein the probe is connected to a pressurized gas and a wiring harness, said wiring harness connected to a power source.

In a further embodiment, the method of treatment wherein a pressurized gas is configured to flow into the first passage.

In a further embodiment, the method of treatment defined to provide suction from the second opening adjacent to the tip and through the second passage.

In a further embodiment, the method of treatment wherein the conductor wire is surrounded by an epoxy along a length of the probe from the proximal end to the distal end.

In a further embodiment, the method of treatment wherein the tip comprises a conductive metal or metal alloy.

In a further embodiment, the method of treatment wherein the tip comprises gallium or a gallium alloy.

In a further embodiment, the method of treatment wherein the first passage and the second passage are attached to an outside portion of the probe or a recess within the probe or are comprised within the probe.

In a further embodiment, the method of treatment wherein the first passage is provided with nitrogen gas.

In a further embodiment, the method of treatment wherein the first passage is provided with a mixture of nitrogen gas and nitric oxide.

In a further embodiment, the method of treatment wherein the first passage is provided with a mixture of nitrogen gas and nitric oxide at a concentration of the nitric oxide of 5,000 ppm and a flow rate of between 0.01 SLPM and 0.15 SLPM.

In a further embodiment, the method of treatment comprising: a suction of between 0.1 SLPM and 10 SLPM of flow within the second passage; and/or a flow of nitrogen gas into the first passage; and/or a flow of a combination of nitrogen gas and nitric oxide, said nitric oxide at between 1,000 ppm and 10,000 ppm, having a standard liter per minute flow of 0.01 SLPM to 0.15 SLPM.

In a further embodiment, the method of treatment comprising administering the cold plasma once a day, twice a day, three times a day, every other day, or on an as-needed basis.

The disclosure, including descriptions, drawings, and claims, describes one or more embodiments of the invention. Many other features, objects, and advantages of the invention will be apparent to one of ordinary skill in the art from the disclosure. Given the disclosure, and in light of the prior art, it is another objective of the invention to improve upon, and overcome the inefficiencies, limitations, and constraints of, the prior art.

BRIEF DESCRIPTION OF THE FIGURES

FIG. 1A is an illustration of a device used to produce cold plasma to apply medically to a patient.

FIG. 1B depicts a plasma probe having a gas and vacuum line adjacent to the plasma probe tip.

FIG. 1C depicts a cross section of plasma probe having a gas and vacuum line adjacent to the plasma probe tip.

FIG. 3A depicts a graphical chart depicting the amount of ozone generated by a plasma probe with various gases, and FIG. 3B depicts only those of $N_2$, $N_2$:NO 0.05, and $N_2$:NO 0.10 concentration without air as a reference to depict the quantity of ozone at appropriate scape.

FIG. 4 depicts a graphical representation of the temperature of a metallic test element being subjected to the various forms of cold plasma for a given duration.

FIG. 7A depicts a variation of an angled cold plasma probe having a bulbous end, and FIG. 7B depicts a straight cold plasma probe with a bulbous end.

FIG. 8A depicts an embodiment of an angled cold plasma probe having a first and a second recess along a portion of the probe, while FIG. 8B depicts a straight probe with recesses.

FIG. 8C depicts a tube attached into the recess of, for example, the recess of FIG. 8B.

FIG. 9A depicts an embodiment of a cold plasma probe wherein the probe comprises two tubes that open at the tip with corresponding recesses at the base, FIG. 9B depicts a variant of the two tubes open at the top with the tubes positioned adjacent to the length of the probe and having a tip recess, FIG. 9C depicts a rear portion of a probe such as the exemplar from FIG. 9A, and FIG. 9D depicts a tip end of a probe with two tubes within the tip body open at the end of the body with the openings having a noncircular opening.

FIG. 10A depicts a further embodiment of a probe, having supply line openings along the rear of the probe, and the tubes along the length of the probe having an arcuate cross-sectional structure, while

DETAILED DESCRIPTION OF THE INVENTION

Figure 2:
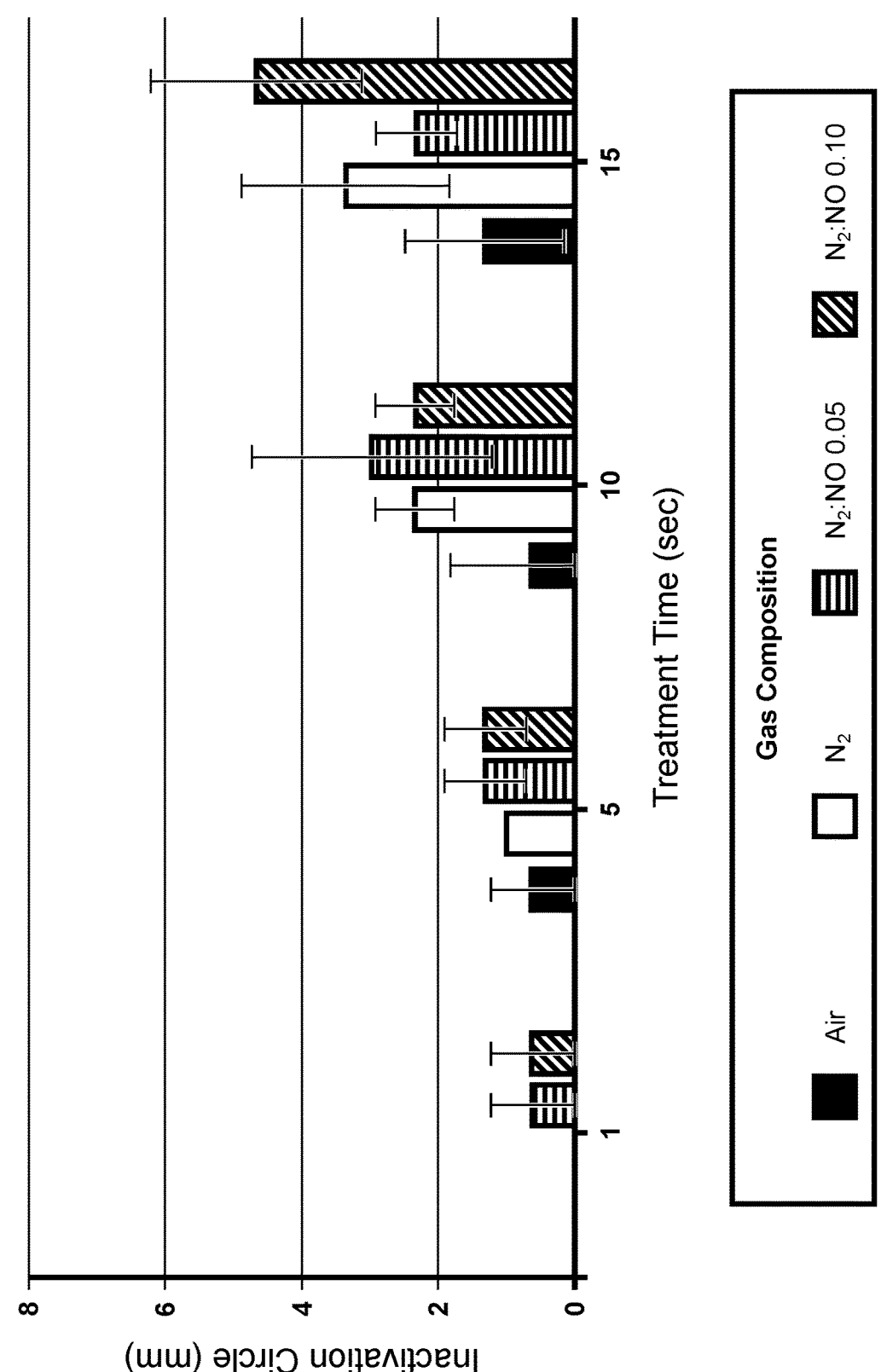
FIG. 2 depicts a graphical representation of treatment time for 1, 5, 10, and 15 seconds for different gases relating to inactivation of *E. coli*.

The disclosures of this patent application, including the descriptions, drawings, and claims, describe one or more embodiments of the invention in more detail. Many other features, objects, and advantages of the invention will be apparent from these disclosures to one of ordinary skill in the art, especially when considered in light of a more exhaustive understanding of the numerous difficulties and challenges faced by the art. While there are many alternative variations, modifications, and substitutions within the scope of the invention, one of ordinary skill in the art should consider the scope of the invention from a review of any claims that may be appended to applications and patents based hereon, including any amendments made to those claims in the course of prosecuting this and related applications.

As used herein the term "pathogens" shall mean microorganisms, bacterial spores, mycobacteria, viruses, nonlipid or small viruses, fungi, vegetative bacteria, and lipid or medium size viruses.

The term "about" means within 10% of a stated number such that "about 100" means between 90 and 110.

Cold plasma is best understood as a gas ionized by the application of high voltage. While there are many ways of generating plasma, known to those skilled in the art, in this application we use 10,000-45,000 V pulses of 0.1 µs to 1 s in duration applied at 100 Hz to 10,000 Hz, and most preferably 17,000-37,000 V pulses of 1-5 µs in duration applied at 1,000 Hz. These high voltage pulses are delivered by the special cables to the probe used by the medical professional. Depending on the gas atmosphere, different reactive species will be created at or near the tissue being treated. Applicant preferably uses nitrogen alone or with a small percentage of nitric oxide. Because the tissue being treated is moist, Applicant also has nonzero quantities of water vapor. Thus, the species generated in this plasma will predominantly be the so-called reactive nitrogen species (RNS):NO, electronically excited NO, electronically excited $N_2$, HNO, $HNO_2$, $HNO_3$, $HNO_4$, and others, including OH radicals, generated from water.

Probes are utilized to generate cold plasma. The unique property of cold plasma, thus, is that we can create high concentrations of these reactive species, which are suitable for then inactivating a wide variety of potential pathogens. Indeed, a wide spectrum of pathogens has been identified as being inactivated via the application of cold plasma for mere seconds.

Disinfection devices disclosed herein include a cold plasma generator. The term "cold plasma" as used herein refers to a plasma which is not in thermodynamic equilibrium, particularly that the temperature of the electrons is much higher than the temperature of ions and neutrals. The term "cold plasma" as used herein is synonymous with the terms "nonthermal plasma" and "nonequilibrium plasma." The cold plasma generators of the disinfection devices disclosed herein may include any generator known to generate cold plasma. Examples of cold plasma generators which may be used for the disinfection devices disclosed herein include but are not limited to glow discharge, corona discharge, atmospheric pressure plasma jet, dielectric barrier discharge, surface discharge, micro-hollow cathode discharge, plasma needle, and low-pressure plasma. Furthermore, the cold plasma generators considered for the disinfection devices disclosed therein may include pulsed cold plasma generators or continuous wave cold plasma generators. Also, the discharge is less uniform and can be hotter, causing tissue damage (which may or may not be desirable) Each of these provides the necessary charges at the tip of a probe, which can be rigid or flexible, of the present disclosure, which in proximity to a body surface (functioning as a charge storing capacitor) allows for production of cold plasma with a simple handheld probe.

Both pulsed and continuous wave dielectric barrier discharge cold plasma generators were used in the development of the disinfection devices disclosed herein and are known to function particularly well with the design considerations discussed herein. Advantages of dielectric barrier discharge cold plasma generators is small size, making them easily configured, and deployed into small spaces and for use with tools, such as the probes detailed herein. Continuous wave dielectric barrier discharge cold plasma generators are advantageous due to their availability and lower costs as compared to pulsed dielectric barrier discharge cold plasma generators. Yet, a disadvantage of employing continuous wave dielectric barrier discharge cold plasma generators is that they generate considerably more ozone in a given disinfection process as compared to pulsed dielectric barrier discharge cold plasma generators. Herein, such ozone production may be contraindicated, and indeed, Applicant has detailed methodologies to virtually eliminate the presence of ozone in the plasma formation, while unexpectedly retaining the antimicrobial effects.

Cold Plasma Application

Preferred embodiments of the present invention involve a low temperature plasma applicator (10) that reliably produces "cold" plasma at near or slightly above room temperature, but not to exceed 50° ° C. to avoid burning of the treated tissue. Embodiments will provide that applicator (10)

can be maneuvered easily to the affected region of a human subject's throat, nose and ear and apply cold plasma by creating a voltage across the probe (18), and wherein the body functions as the charge storing capacitor, allowing formation of the cold plasma, and in doing so, creation of the concentration of reactive species needed and desired for the therapeutic treatments. The prior art, by contrast, created cold plasma by having an opposing electrode that allows for creation of cold plasma between two electrodes.

The embodiments detailed herein will allow for therapeutic application of cold plasma to patient populations in need of treatment thereof. For example, the treatment methods will be particularly suitable to the population who experience chronic tonsillitis or other ailment that want to avoid costly surgery to remedy. Preferred embodiments of the present invention alleviate the issue by offering an alternative treatment that many people would find preferable to the standard treatment options of antibiotics or surgical procedures. The features that will be described in detail below combine to offer a more convenient form of treatment using the applicator (10).

Figures 1A, 1B, 1C:
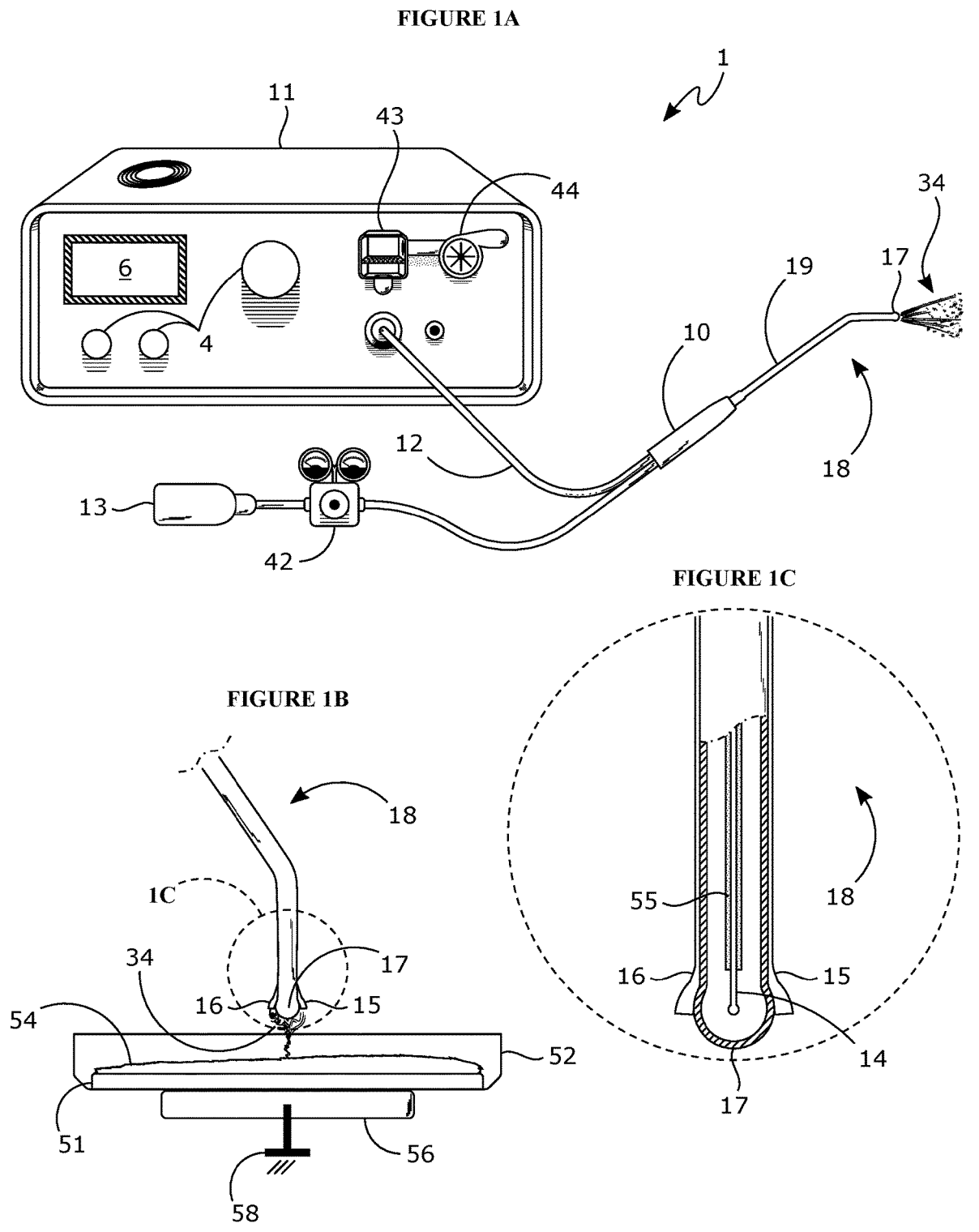

Turning to FIG. 1A, there is shown a preferred embodiment of a device (1) the cold plasma applicator (10). Preferred embodiments of the applicator (10) generate quantities of cold plasma (34) by generating a charge at the tip (17) of the probe (18) via the conductor wire (14) sufficient to generate the cold plasma (34). The conductor wire (14), for example, those depicted in FIGS. 7-10 as nonlimiting examples, generally create the cold plasma (34) at a tip (17) and not along a portion of the shaft (19) so that precise application of cold plasma (34) can be delivered.

The cold plasma applicator (10) comprises an insulated conductor wire (14) such that the conductor wire (14) is insulated (55) along the length of the shaft (19) of the probe (18), and wherein the end of the insulated conductor wire (14) is provided in a reactive tip (17) such that the cold plasma (34) is generated at only the tip (17). One such example of the reactive tip (17) is that the tip (17) is filled with gallium, which is liquid at about 40° C., and, in connection with the conductor wire (14) which is noninsulated at the end of the conductor wire (14), creates the charge sufficient to generate the cold plasma (34). The tip (17) may be filled with another conductive metal or metal alloy, gallium and alloys with gallium, or a similar metal having a low melting point temperature as preferred.

As depicted in FIG. 1A, and further detailed in additional embodiments, the applicator (10) holds the probe (18) and wherein a vacuum line (15) and a gas line (16) have openings adjacent to the tip (17). The gas line (16) is connected, such as via a connection harness (12) to a compressed gas (13), which delivers a quantity of gas at a specific flow rate. Preferably, this is utilized in conjunction with a regulator (42) that controls the quantity and flow rate of the gas. Simultaneously a vacuum pump (44) provides suction through the vacuum line (15) to pull gas from the tip (17). The regulator (42) and vacuum pump (44) may optionally operate with a filter (43). The two features of the gas line (16) and the vacuum line (15) work in concert to create improvements to the generated cold plasma (34), which is detailed herein. Namely, the mixture of gas provides for an increase in efficacy using certain gas mixtures, reduces the working temperature of the plasma at the target tissue, and dramatically reduces the production of ozone. The combination of maintaining and unexpectedly increasing the efficacy of treatments while simultaneously virtually eliminating the quantity of ozone production yields an unexpected result that provides for unique methods of treatment within the oral and nasal cavity that would be unavailable with typical plasma treatments due to the presence of and manufacture of ozone.

The probe (18) and applicator (10) are connected to a control box (11) which provides for management of the electrical current, as well as operating and controlling vacuum and gas flow in certain embodiments. Essentially, the control box (11) may serve as a power supply, powering the probe (18), but may also provide for control of gases, vacuum, and other features which can be optionally controlled by the control dials (4) which may be desirous to be displayed on the device display (6). Parameters are adjusted and current operating parameters are displayed on the device display (6). Different modes of action can be selected in the control box (11) via the control dials (4) and can be used to customize the intensity or temperature of the cold plasma so that a number of medical treatments can be achieved by altering voltage, wavelength, among other parameters. For example, cold plasma (34) from the applicator (10) can be used in the removal or reduction of biofilm from tissue, reduce the size of tissue, or in some cases, selectively injure tissue to achieve medical results. Those skilled in the art will recognize that a number of medical applications can be achieved by utilizing cold plasma and these are just some of the nonlimiting examples for illustrative purposes.

The applicator (10) is connected to the control box (11) via a connection harness (12), which allows the operator to easily manipulate the applicator (10) during operation. Within connection harness (12) there is at least one electrical connection, which can be multiple wires to complete that connection and optionally, a vacuum line (15) and/or a gas line (16). In order to create plasma (34) at this temperature, a compressed gas (13) such as an inert or "noble" gas source and the like is used such as helium, nitrogen, nitric oxide, argon, and mixtures of gases in combination with such gases. Applicant identifies that a plurality of different noble gases and nontoxic gases may be suitable. A conductor wire (14) within the instrument is used to ionize the gas from the compressed gas source (13) and generate dielectric barrier discharge plasma. An integrated vacuum line (15) is utilized to capture any excess ozone particles that are generated that can cause harm to the patient. Here, vacuum line (15) means that suction is being provided to pull gases from the tip (17).

Preferred embodiments of the probe (18) are shaped in a manner to allow the physician or technician to maneuver easily in the desired region of the human subject in tight spaces such as the mouth, throat, esophagus, nasal cavity, paranasal sinuses, and ear. The probe (18) can be a single use, disposable probe or it can be a multiple use probe capable of being repeatedly sterilized. The type of probe will be dictated by the medical treatment being provided. In one, nonlimiting example, a probe (18) is comprised of a conductive wire (14) that is coated with any type of insulation (55). The probe (18) may optionally be filled with degassed epoxy, or similar material, to limit movement of the conductive wire (14) within the probe (18). In a preferred embodiment, the epoxy filled probe is then placed in a high-pressure chamber to further compress the epoxy as it cures to eliminate trapped air. The epoxy can fill some or all of the internal opening (78) from e.g., FIG. 9C, and retain access to the conductor wire (14) such than an electronic connection can be made to provide the necessary power source. As those persons skilled in the art will readily recognize, the device (1) shown is for illustrative purposes and many other configurations of the device (1) can be used to achieve the same result such as with a separate control element like a foot pedal to operate.

FIG. 1C is a cross-sectional detail of one nonlimiting configuration of probe (18) showing the more specific location of gas line (16) and vacuum line (15) as they run along probe (18) terminating at tip (17). Alternatively, gas line (16) and vacuum line (15) can terminate closer to or further from tip (17). Within probe (18) is housed a conductor wire (14) optionally covered in insulation (55).

FIG. 1B provides an example of the design of a testing apparatus. Here, the probe (18) is vertically mounted, with adjacent gas line (16) and vacuum line (15), being generally provided at a distance of about 1 mm to a sample Petri dish (52) with a layer of microorganisms/bacteria (51) grown on an agar layer (51) within the Petri dish (52). This setup was used to test the efficacy of the treatment on a sample species. The sample was prepared using a standard agar solution (51) to grow microorganisms/bacteria (54), specifically *E. coli* O157:H7 on Lysogeny broth. The total concentration of *E. coli* was $2 \times 10^7$ colony-forming units (cfu) per milliliter of Lysogeny broth (LB). A voltage of 27 kV at 1,000 Hz was applied via the probe. All tests were performed at room temperature with the Petri dish (52) sitting on a grounding plate (56) that is connected to a grounding wire (58).

FIG. 2 is interesting for several reasons. First, is that it is widely understood that oxygen is generally necessary to provide sufficient quantities of reactive species. However, in view of FIG. 2, what is clear is that at a time period of just one second, the combinations of nitrogen gas ($N_2$):nitric oxide (NO) each provided at least some inactivation, while air and $N_2$ alone produced no measurable inactivation. At a time of five seconds, all gases provided at least some inactivation, however, the combination of the $N_2$:NO mixtures yielded larger inactivation circles. This continued again with both the ten- and fifteen-second experiments. In the case of a ten-second treatment, notably, all of the $N_2$ gases were dramatically and unexpectedly superior in inactivation than treatment with air alone. Accordingly, in all cases, the use of nitrogen gas, alone or in combination with NO is at least equivalent in its inactivating power as compared to ambient air, and indeed, on average is superior to ambient air in all cases. The fact that the $N_2$ gas, alone or with NO, was even equivalent to the air mixture, yet alone superior to the air mixture was an unexpected surprise regarding the improved efficacy of treatment using the nitrogen gases.

This study was then repeated with a second bacterial species to ensure that the cold plasma reacted across different species as was previously reported in the literature, but also that it would retain efficacy with the nitrogen gas species. Table 1 depicts this test, and further details inclusions of NO at a lower and higher concentration.

TABLE 1

| Time (sec) | Air | $N_2$ | $N_2$ + 0.01 NO | $N_2$ + 0.05 NO | $N_2$ + 0.10 NO | $N_2$ + 0.15 NO |
|---|---|---|---|---|---|---|
| 1 | 0.0 ± 0.0 | 0.0 ± 0.0 | 0.0 ± 0.0 | 0.3 ± 0.6 | 1.3 ± 0.6 | 0.7 ± 0.6 |
| 5 | 0.7 ± 0.6 | 1.0 ± 0.0 | 1.0 ± 0.0 | 1.7 ± 0.6 | 1.7 ± 0.6 | 1.3 ± 0.6 |

TABLE 1-continued

| Time (sec) | Air | $N_2$ | $N_2$ + 0.01 NO | $N_2$ + 0.05 NO | $N_2$ + 0.10 NO | $N_2$ + 0.15 NO |
|---|---|---|---|---|---|---|
| 10 | 1.7 ± 0.6 | 2.0 ± 0.0 | 2.3 ± 0.6 | 2.3 ± 0.6 | 3.7 ± 0.6 | 2.7 ± 0.6 |
| 15 | 2.0 ± 0.0 | 2.7 ± 0.6 | 3.3 ± 0.6 | 3.7 ± 1.2 | 4.3 ± 1.2 | 3.7 ± 0.6 |

What is immediately obvious from the data is that the presence of NO within any sample increases efficacy. Indeed, even the lowest concentration of NO provides a trend toward higher inactivation, and reaching toward quantities of 0.05 NO provides a significant increase in the efficacy. However, simultaneously, Applicant notes that the presence of more NO is not simply additive. Indeed, increasing the concentration up to 0.15 NO, actually reduced efficacy meaningfully from the 0.10 NO concentration with $N_2$. Accordingly, in certain embodiments, limiting the NO concentration from 0.01 to 0.15 is advantageous.

Figure 3A:
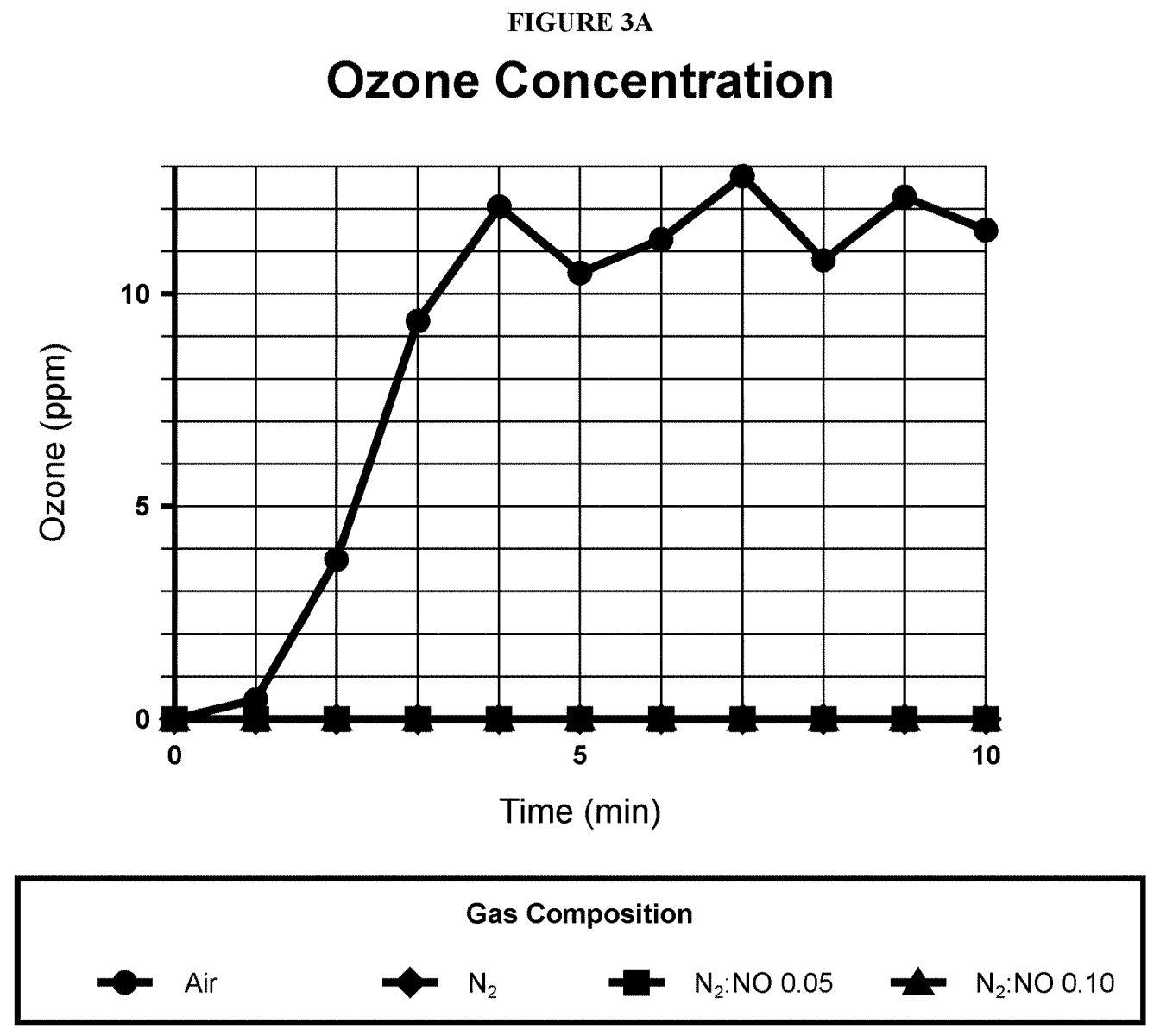
Figure 3B:
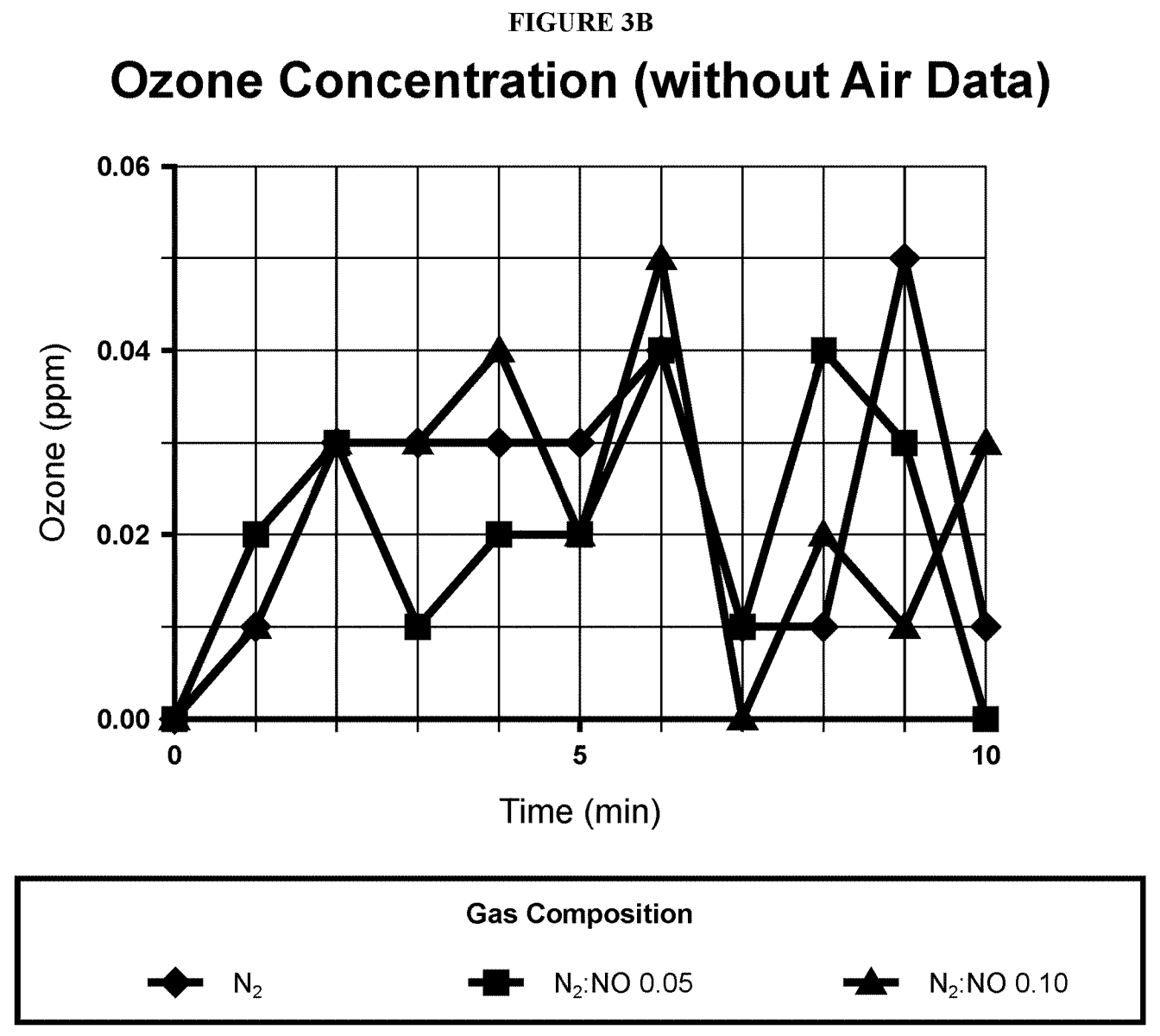

One of the major benefits of using nitrogen gas or a mixture of nitrogen gas and nitric oxide ("NO"), instead of ambient air, is the reduction in the presence of oxygen and thus dramatically reducing the formation of ozone from the cold plasma. Because the treatments are indicated and desired in the nose and mouth, patients would inherently be exposed to ozone. FIG. 3A depicts a graphical representation showing the concentration of ozone in parts per million ("ppm") over time when comparing four different gases. FIG. 3B is provided as a supplement to show data and omitting the "air" as one of the gases, due to the significant differences in the ozone production. Indeed, when using air alone, in FIG. 3A it can be seen that at two minutes, ozone ppm is measured at about 4 ppm, and then at three minutes, the concentration of ozone reaches its near maximum concentration of between about 10-13 ppm, which appears to somewhat stabilize at between three to ten minutes of time.

In contrast, when looking at FIG. 3B, ozone concentration again appears to stabilize at its maximum around three to four minutes, but this level is at or below 0.05 ppm, and at a time of three minutes is below this at about 0.03 ppm for all of the nitrogen-based gases tested. This is equivalent to 100 times the difference in the ozone measurement when comparing the air generated cold plasma to those created with the compressed gases. The amount of ozone produced in such examples is below the standards set by the EPA established in 2015, which is 0.070 ppm. This provides a unique antimicrobial solution that heretofore was unavailable due to the toxic presence of ozone, at levels that may be effectively safe for therapeutic treatment.

Thus, Applicant has created a device that generates sufficient amounts of cold plasma that improve upon the inactivation properties of cold plasma as compared to creating cold plasma in ambient air, all the while dramatically reducing the concentrations of ozone produced, thus increasing safety of treatment within the ear and especially in the nose and throat.

Method of Use

Returning to FIG. 1A, the probe (18) of the device (1) possesses a tip (17) at the distal end of the applicator (10), which creates cold plasma (34). The probe (18) comprises a conductor wire (14) extending from a proximal end to a distal end and having a tip (17). The device is shaped such that a practitioner holding the applicator (10) can place the tip (17) into the mouth or into the nasal passages and, after activating the device (1) by selecting the desired voltage for the given treatment using the control dials (4) and the device display (6), create cold plasma (34) at the tip (17). The cold plasma (34) generates high concentrations of reactive species, which react with microbial species to inactive them.

Interestingly, the plasma created by the present disclosure is referred to as "cold" plasma. This is because the formation of the plasma is warm but does not reach temperatures that could cause major burning, such as temperatures over 70° C. or higher. However, even creating temperatures as high as 45° C. can quickly cause discomfort or even burns. This is especially true with sensitive skin, such as those within the mouth or nasal passages. Furthermore, even if the temperature is only at 40° C., such temperature can cause discomfort to a patient.

Figure 4:
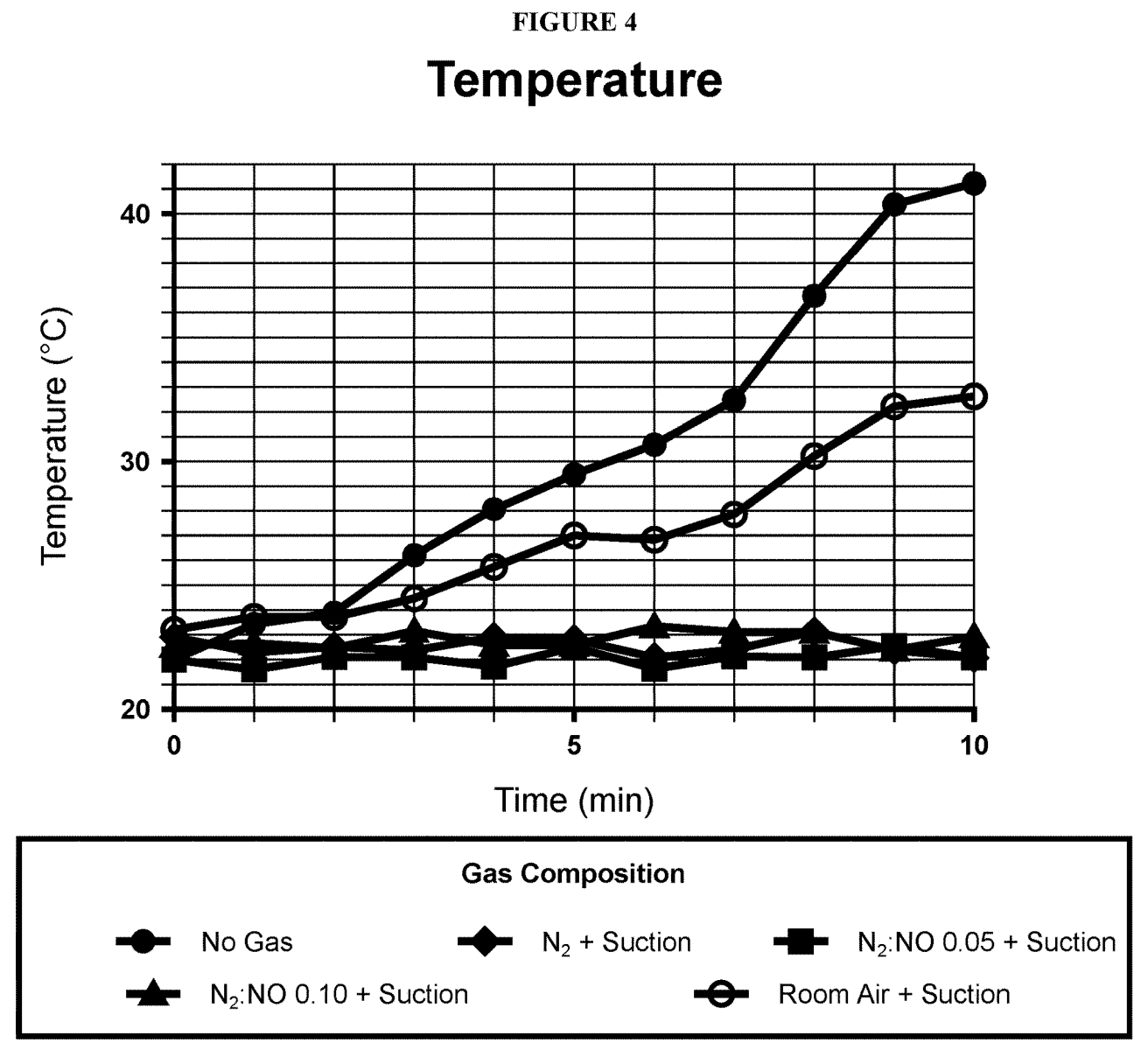

Applicant tested the temperature of the cold plasma, by testing its ability to heat a small metal plate placed one millimeter from the cold plasma and holding the device for up to ten minutes to determine the differences in temperature among the various gas mixtures being utilized. What was fascinating is that, in addition to the greater efficacy identified by using nitrogen gas or nitrogen and NO, a dramatic and unexpected reduction in temperature was realized. Indeed, after even a few minutes, the plasma created by using room/ambient air, with or without suction/vacuum, was dramatically different than those using any of the nitrogen mixtures. FIG. 4 clearly depicts that while temperature is relatively similar at inception and at one minute, by the second minute, where the nitrogen gas examples were almost perfectly stable at between 22° C. and 23° C., the air from the room, or simply without air, already showed an increase over this stable temperature and continued to rise significantly at each minute. When the device is then utilized within the nasal passages, the rapid increase in temperature may be sufficient to cause discomfort or damage these sensitive tissues with the air examples. However, with nitrogen gas, or mixtures using nitrogen gas, the temperature remains far below any threshold that could cause pain, discomfort, or burning of the tissue. Indeed, when looking at FIG. 4 at ten minutes of time, the temperature for the probe without gas is nearly 20° C. higher than when using nitrogen alone or in mixture.

Figure 5:
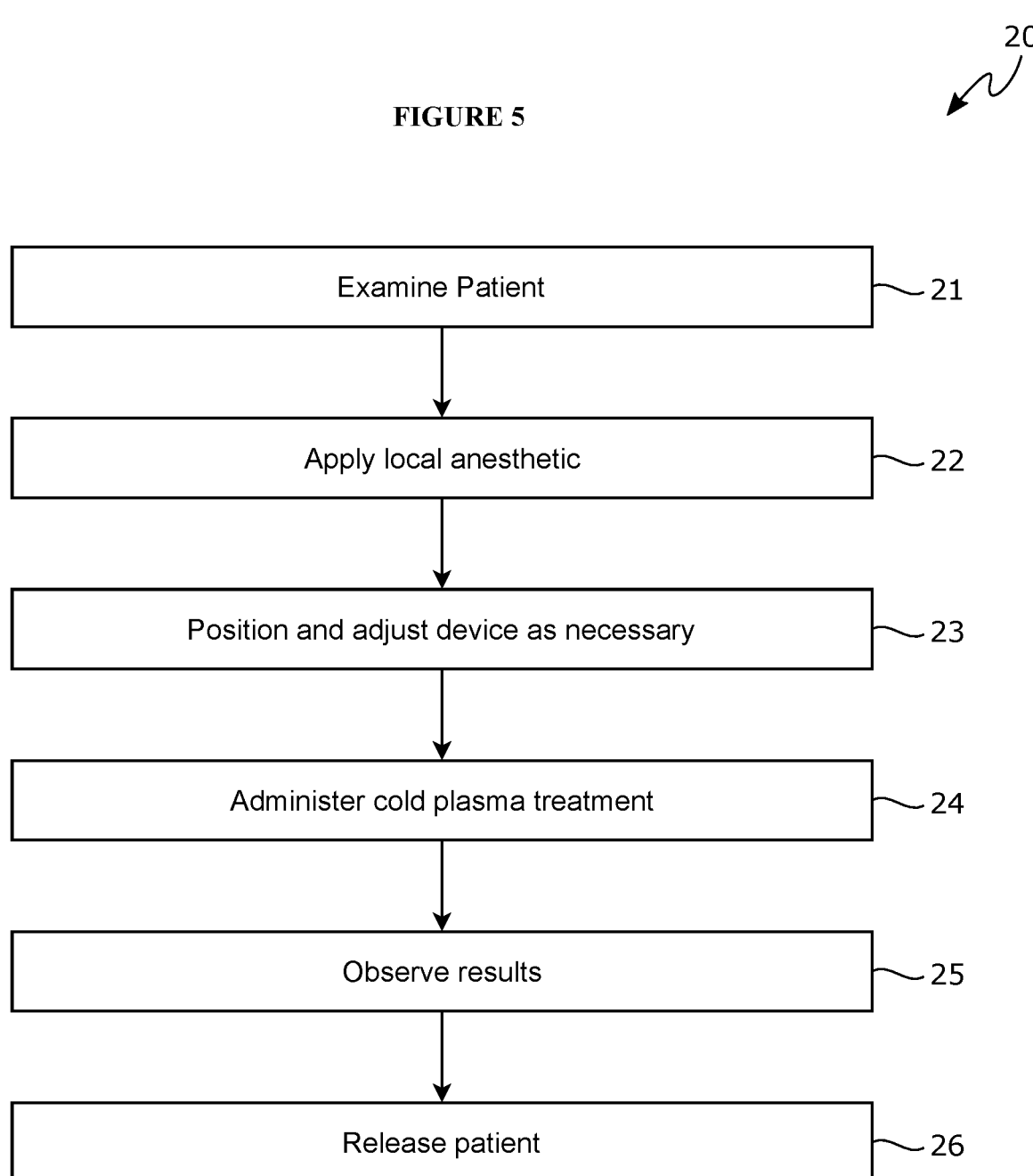
FIG. 5 depicts a flowchart of a method for treating a patient with cold plasma in the throat or nose.

Turning to FIG. 5, which shows a flowchart (20) of the method in when the device (1) (from FIG. 1A) is utilized for treatment of the throat. In the first step (21), the patient is examined by the physician to determine the correct course of treatment. Then, if necessary, the patient is treated with a local anesthetic, in the region that is to be treated in the next step (22). Once the anesthetic has set in, the device (1) (from FIG. 1A) is adjusted to the desired operating parameters and positioned to effectively treat the desired region in the following step (23). Then, the device (1) (from FIG. 1A) is used to treat the tissue for the appropriate amount of time while providing a vacuum for excess ozone that is generated in the next step (24). Next, the results of the treatment are observed by the physician to determine the next course of action in the following step (25). Finally, the patient is released if no further treatment is needed in the last step (26).

Figure 6:
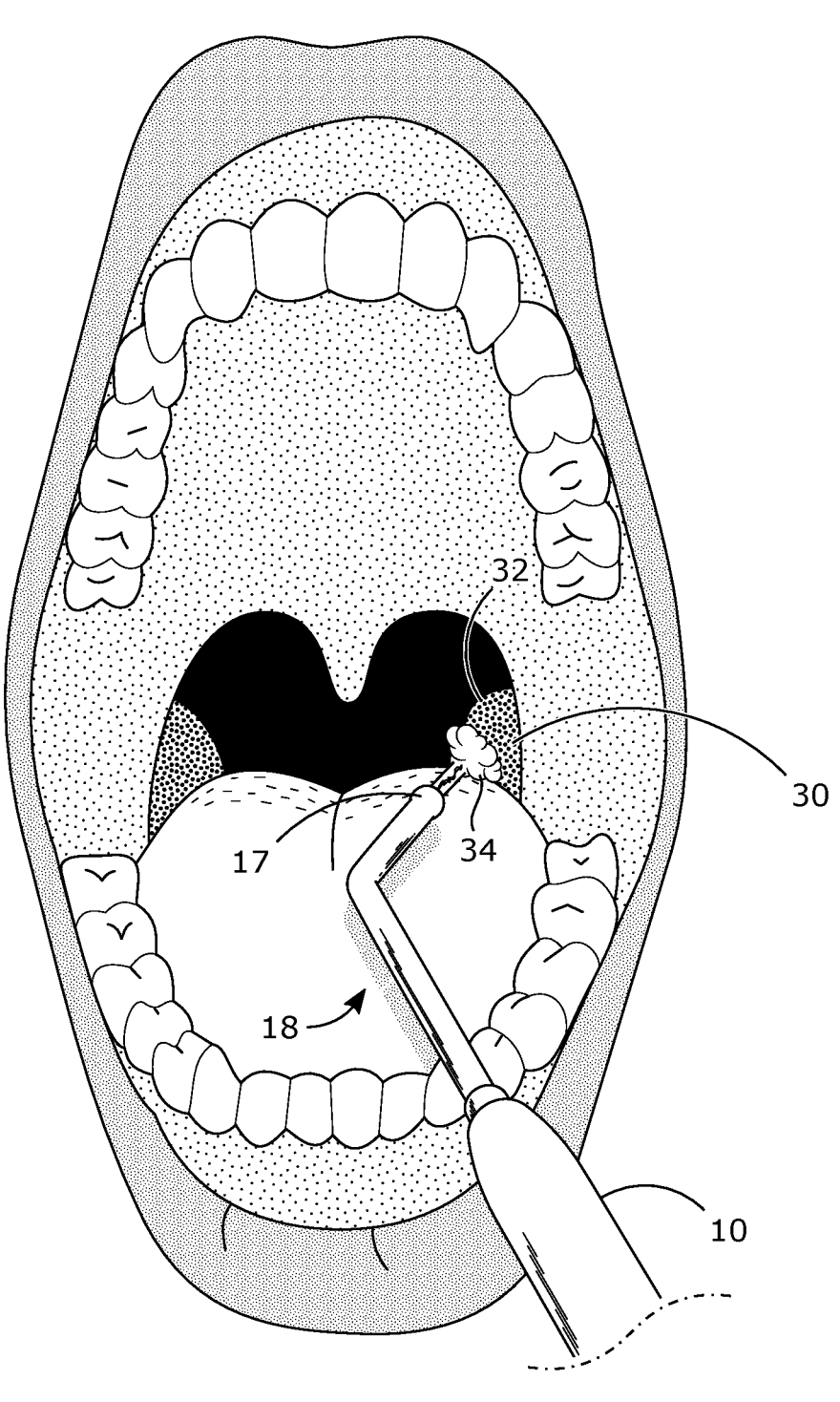
FIG. 6 depicts a representation of a treatment of the tonsils using a cold plasma device.

Turning to FIG. 6, which illustrates the applicator (10) comprising a probe (18) with a tip (17) treating the tonsils

(30) of a patient. Once the applicator (10) is positioned and calibrated, the conductor wire (14) (from FIG. 1C) provides the necessary electrical charge to create the cold plasma (34) between the probe tip (17) and the tissue, thus applying cold plasma to the affected area, in this case, the tonsils (30) of the patient. For this procedure, the control dials (4) (from FIG. 1A) are set to allow the cold plasma (34) that is generated to be at room temperature that is adequate to sterilize and reduce or remove the microorganisms/biofilm (32) surrounding the tonsils (30) but avoids causing injury or discomfort to the tissue. Cold plasma (34) is applied to the tonsils (30) to treat the microorganisms/biofilm (32) that have developed on the tonsils (30). Those skilled in the art will recognize that the figure is for illustrative purposes and the applicator device may be in a different configuration or shape.

One of the key benefits of the cold plasma treatment is that it is universally antimicrobial. Thus, treatment of, especially diseases of the ear, nose, and throat, which may be highly variable to the given pathogen, the cold plasma can treat such broad pathogens instead of having singular or limited function over one species or class such as viral, bacterial, microorganism, and/or fungal. Cold plasma has been shown to kill numerous pathogens, a nonlimiting list is provided in Table 2.

TABLE 2

| Pathogen | Plasma Type |
| --- | --- |
| Campylobacter | DBD (Dielectric Barrier Discharge) |
| Clostridium perfringens | Plasma Jet, Microwave Cold Plasma |
| E. coli | DBD, Afterglow Discharge, Uniform Glow Discharge |
| Listeria | DBD, Afterglow Discharge, Uniform Glow Discharge |
| Norovirus | DBD (Surface Micro Discharge) |
| Salmonella | DBD, Afterglow Discharge, Uniform Glow Discharge |

The benefit of such broad spectrum antimicrobial material is immense. Indeed, many other species are inactivated or destroyed by cold plasma. Certain studies have shown that nonthermal plasma can inactivate 99.9% of airborne viruses through releasing energetic molecules, to kill the viruses in less than a second. Microorganisms such as bacteria are inactivated by destruction of their cell wall. Fungi are also inactivated with cold plasma, though they may be somewhat less sensitive than microorganisms, viruses, and bacteria and may require additional time for inactivation. Nonetheless, spores were inactivated after treatment times of as little as one second for certain Aspergillus niger, Penicillium citri- num, Cladosporium cladosporioides, and Chaetomium sp. species. Certain Candida sp. were also inactivated at high rates after treatment times of less than ten minutes. There- fore, use of the materials allows for a broad inactivation of a wide variety of microbial species.

FIGS. 7A and 7B depict two different probe examples, with the probe (18) in FIG. 7A being curved before it terminates at tip (17) and the probe (18) in FIG. 7B having a straight orientation until it terminates at tip (17). Both probes (18) in FIGS. 7A and 7B comprise a conductor wire (14) extending from a proximal end to a distal end and having a tip (17) and further comprise a receiving end (64) that connects the probe (18) to applicator (10) (from FIG. 1A). Accordingly, Applicant conceives that the particular shape of the probe may include a straight or a bent shape to better allow for access to a desired treatment area.

FIGS. 8A and 8B depict an example of a probe (60, 62) having a gas exterior recess (65) and a vacuum/suction exterior recess (66), which run substantially down the length of the probe (60, 62) with FIG. 8A being a curved recessed probe (60) and FIG. 8B being a straight recessed probe (62). In FIGS. 8A and 8B, the gas exterior recess (65) and the vacuum/suction exterior recess (66) are shown opposite of one another, but they could be in any configuration on the probe including stacked on top of one another so that only one recess is needed. The gas exterior recess (65) and the vacuum/suction exterior recess (66) are in place to allow for a small diameter tube (68) (from FIG. 8C) to be affixed to the probe. The small diameter tube (68) (from FIG. 8C) can then be utilized to transmit gases (such as the compressed gas (13) (from FIG. 1A) both under pressure and then pulling from a vacuum/suction (such as from the vacuum pump from FIG. 1A). It is understood that where there are two different tubes (68), one tube will transfer gases under pressure, which will release at the recessed tip (67) end of the curved recessed probe (60) or the straight recessed probe (62). The second tube, such as the vacuum line (15) (from FIG. 1A) will then be connected to a vacuum pump (44) (from FIG. 1A) and will pull whatever air or other gas mixture that is present at the recessed tip (67) end. Both the curved recessed probe (60) (from FIG. 8A) and the straight recessed probe (62) (from FIG. 8B) have a receiving end (64) that connects the probe (18) to applicator (10) (from FIG. 1A).

FIGS. 9A, 9B, 9C, and 9D depict examples of a through conduit probe (70) that contains an internal passage having a first passage and a second passage and a conductor wire (14) extending from a proximal end to a distal end and having a tip (17). Turning to FIG. 9A, one passage is the gas through conduit (71) and the other passage is the vacuum through conduit (72). In FIG. 9A, these conduits are shown opposite each other on the through conduit probe (70) however, the gas through conduit (71) and the vacuum through conduit (72) can be in any configuration within through conduit probe (70), and while through conduit probe (70) is shown as being straight in FIG. 9A, one skilled in the art will appreciate that it can be in any shape and/or configuration necessary to perform the medical procedure including but not limited to being bent, rigid or flexible. These two passages/through conduits have the same general functionality as the tubes (68) from FIGS. 8A, 8B, and 8C in that one passage/through conduit functions as a line to send air and/or gas to the tip (17), with the air and/or gas being pressurized to flow at a particular flow rate using the regulator (42) (from FIG. 1A) which may optionally engage the filter (43) (from FIG. 1A). This passage/conduit is generally referred to as the gas through conduit (71). The air and/or gas leaves the through conduit probe (70) via the gas exit (74a) at the tip (17). The opposite line then pulls the air/gas expelled from the gas exit (74a) at the tip (17) via the vacuum entry (75a) into the vacuum through conduit (72). The through conduit receiving end (73) of through conduit probe (70) connects the through conduit probe (70) to applicator (10) (from FIG. 1A). In FIG. 9A, the gas and/or air flow directly though the gas through conduit (71) and the vacuum through conduit (72) however, one skilled in the art will recognize that it may be advantageous to line these through conduits with other materials or run tubes or supply lines or return lines within the conduit. Thus, the designs are not so limited, but detail one solution to the problem of providing a pressurized particular gas to the tip via a supply line and pulling gas from a point adjacent to the supply line.

This allows for creation of the desired reactive species, limits ozone production, and pulls created gases back via the suction side.

FIG. 9A in particular shows the tip (17) end of through conduit probe (70) that has a rounded end. The gas exit (74*a*) and the vacuum exit (75*b*) are placed on opposing sides of the tip (17), with a rounded shape. By contrast the rectangular gas supply (76) and the rectangular vacuum (77) of FIG. 9D are a more oval or rectangular shaped inlet and outlet. The purpose of the shape change is to encourage the spread of plasma at the tip (17), creating a broad treatment area. Again, rectangular gas supply (76) and rectangular vacuum (77) are shown opposite one another in FIG. 9D, however one skilled in the art will recognize that they can be in any configuration that will optimally deliver plasma to the treatment area and while the gas through conduit (71) and the vacuum through conduit (72) as shown as straight and opposite one another, these can also be in any shape, location and/or configuration including spiraling within through conduit probe (70).

FIG. 9C depicts the rear of the through conduit probe (70) of FIG. 9A where the probe terminates into the through conduit receiving end (73). The through conduit receiving end may optionally be threaded to connect it to the through conduit probe (70) and the applicator (10), or it can be attached via adhesive, or it can be molded so that the probe, receiving end and applicator are one piece, or the three components can be attached together via any other means generally known in the art. A suitable supply line can be inserted into the gas entry (74*b*) hole, and a second return line can be inserted into the vacuum exit (75*b*) hole. The internal opening (78) will hold the conductor wire (14) and will accept a banana clip style plug, to create the electrical contact between the conductor wire (14) with optional insulation (55), the banana clip (not shown) and the control box (11) (from FIG. 1A). Notably, the particular design of the banana clip can be virtually any connector known to those of ordinary skill in the art. While this embodiment has described a supply line, a return line and/or a tube being inserted into the gas entry (74*b*) and the vacuum exit (75*b*), gas/air can flow directly through the gas through conduit (71) and the vacuum through conduit (72) without the use of an intermediary line or tube.

FIG. 9B depicts channel probe (80) being a variation wherein the orifice(s) that allows for the passage of air/gas from the compressed gas (13) (from FIG. 1A) and the vacuum suction from the control box (11) (from FIG. 1A) to the channel tip (84) is printed, molded, machined, or otherwise affixed to the outer side of the channel probe (80). As shown in FIG. 9B, the exterior gas supply line channel (82) and the exterior vacuum line channel (83) are on the outside surface of channel probe (80). The gas/air stream may flow directly within exterior gas supply line channel (82) and the vacuum suction can remove the emitted air/gas directly through the exterior vacuum line channel (83). Alternatively, as shown in FIG. 9B, a vacuum line (15) can run through exterior vacuum line channel (83) to pull air/gas from the treatment site through the channel probe (80), through the shaft (19) of the applicator (10), and into the control box (11) all shown in FIG. 1A. Similarly, a gas line (16) can run through the exterior gas supply line channel (82); while mostly obscured in FIG. 9B, it is substantially in the form shown for vacuum line (15). While exterior gas supply line channel (82) and exterior vacuum line channel (83) are shown opposite each other in FIG. 9B, they can be in any shape or configuration as needed to perform the necessary medical treatment. This can include vacuum line (15) and gas line (16) sharing a single exterior channel. Additionally, while one exterior gas supply line channel (82) and one exterior vacuum line channel (83) are shown on channel probe (80), one skilled in the art will appreciate that another embodiment may include only one of the aforementioned channels and/or lines. Alternatively, there can be any multiple of exterior gas supply line channels (82) and exterior vacuum line channels (83) and these need not be in even pairs. For example, channel probe (80) may contain two exterior supply line channels (82) and four exterior vacuum line channels (83) or n exterior supply line channels (82) and n exterior vacuum line channels (83), as nonlimiting examples.

Furthermore, the channel tip (84) possesses a channel tip recess (81) that is defined to encourage air to flow from the gas line (16) around the channel tip (84) and into the vacuum line (15). This channel tip recess (81) encourages a more even or different disbursement of the plasma created at the channel tip (84). While FIG. 9B shows only one channel tip recess (81) in a particular size and shape, it should be understood that there can be any plurality of channel tip recesses in any size, shape and/or configuration so as to deliver the appropriate dosage of plasma to the treatment site.

Figure 10A:
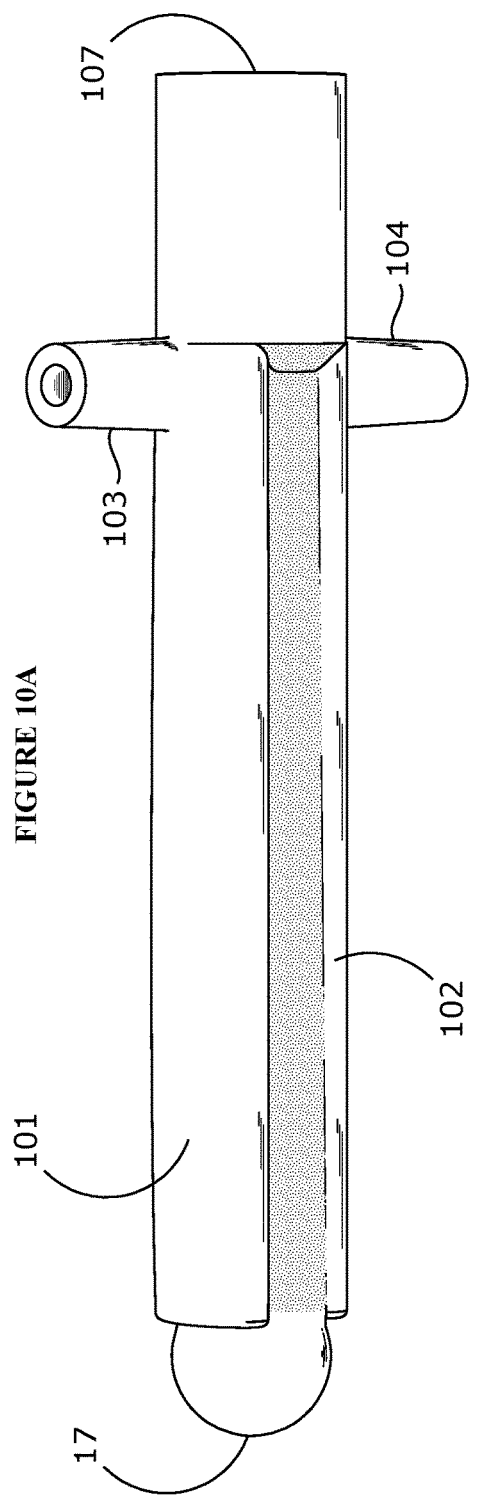

FIG. 10A depicts a further example of a probe, having a left channel (101) and a right channel (102), these channels originate prior to the channel receiving end (107) and run the length of the probe to the tip (17). Left channel (101) connects to left port (103) and the right channel (102) connects to the right port (104). The left channel (101) and right channel (102) are used to move gas/air to the tip (17) and remove gas/air from the treatment site via vacuum. Either channel can be used for either purpose, and while only two channels are shown opposite one another on the probe it should be understood that there can be any plurality of channels in any configuration to optimize the delivery of plasma to the treatment site including having two channels stacked on top of one another. Additionally, while FIG. 10A shows left port (103) and right port (104) perpendicular to the probe, these ports can be at any angle to optimize performance. Left port (103) and right port (104) may terminate in any type of configuration generally known in the art that will allow the port to connect to the gas line (16) (from FIG. 1A) or the vacuum line (15) (from FIG. 1A), such as, but not limited to, threads, a compression fitting, a union, a flange, a flare, a quick connect or any other coupling system generally known in the art.

Figure 10B:
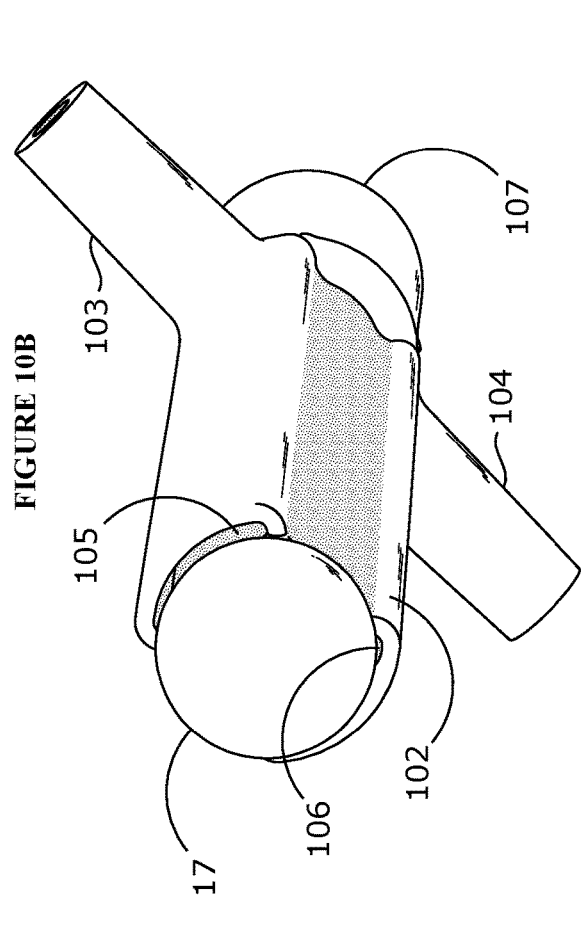
FIG. 10B depicts the probe of FIG. 10A from a front angled view and depicting the arcuate cross-sectional structure.

As shown in FIG. 10B, left channel (101) terminates at left flat opening (105) and right channel (102) terminates at right flat opening (106). These channels connect to the flat openings, one on each side of the probe, which run along the length of the probe to the tip (17). The left flat opening (105) and the right flat opening (106) encourage a greater flow of air/gas in both the supply and suction side of the channels, while maintaining a low profile to the overall shape of the probe. FIG. 10B shows the tip (17) end of the probe with the left flat opening (105) and the right flat opening (106) each having a slightly arcuate shape at the opening end.

In this manner, each of the features allows for the production of certain species, such as ozone, to be captured and pulled away from the tip by use of the suction side. A filter (43) (from FIG. 1A), such as one comprising activated carbon, can be placed in line on the suction side, to capture ozone or other produced materials that are not desirable to be spread from the suction side tube. The optional filter may be placed anywhere that allows the air to be filtered as desired for use.

Interestingly, a further element is created by the application of pressurized gas being deployed to the tip (17) of a probe, such as depicted in FIG. 1B. Applicant took a photograph at high speed of the plasma created in an example of air, but no suction, and compared that to the $N_2$:NO 0.1 example with suction. Interestingly, the air example provided a beam of plasma that was merely 0.5 mm wide. This creates a "hot" spot for plasma formation and treatment. In comparison, providing the flow of the nitrogen and NO mixture, with suction, generated a plasma beam that was five times wider at 2.5 mm. This creates a broad, uniform treatment area of plasma, yet based on the studies herein, also provided significantly greater results in inactivating the microbes being treated. This plasma spread was an unexpected benefit of adding the controlled flow of gas at the tip that is combined with greater efficacy, lower temperature, and greatly reduced ozone formation.

A number of treatments can be achieved with the device (1), and the ability to safely and effectively remove microorganisms, bacteria, and/or biofilm (32) from tissue has been detailed above. However, the medical applications for cold plasma (34) extend to a variety of treatments in the sensitive areas of the nose, mouth, and ears. Halitosis can be treated with the device by applying cold plasma (34) treatment to the affected region in the patient's mouth or esophagus. Barrett's esophagus can be treated by selectively injuring the desired region with cold plasma (34) of the esophagus via transnasal esophagoscopy.

TREATMENT OF TONSILS: Tonsils (30) (from FIG. 6) are a set of lymphoid organs facing into the aerodigestive tract. Tonsils refer to the adenoid tonsils, tubal tonsils, palatine tonsils, and the lingual tonsils. The tonsils in the rear of the throat are most often a primary cause of tonsilitis. Tonsillitis refers to an infection of the tonsils and frequently includes significant swelling of these structures. Tonsillitis is most frequently caused by viral infections; however, the infection may also be bacterial or caused by other microorganisms. Bacterial infections, like those of *streptococcus*, RSV, and other common bacteria and viruses all lead to the same inflammation, pain, and infection, which may become recurrent to some patient populations. Using the device (1) as described herein, a practitioner may follow the flowchart of FIG. 5, and, as in the exemplar of FIG. 6, take a probe (18) adjacent to the tonsils (30) and apply the cold plasma (34). A practitioner may move the probe tip (17) around the infected area of the tonsils (30) to allow for an even distribution of cold plasma (34). As part of the treatment plan, the practitioner places the probe (18) at a distance from the tonsils (30) so that the tip (17) does not directly come in contact with the tonsils (30) but not so far away from the tonsils (30) so that the tip does not generate the correct amount of cold plasma (34), for example, at a distance that is greater than zero mm from the tonsils but less than five centimeters ("cm") from the tonsils. The device (1) and probe (18) have a distinct advantage over the prior art in that functionality is improved because the probe's proximity to the patient's body (e.g., infected area or tissue) allows the body to function as the charge storing capacitor to create cold plasma thus obviating the need for a second electrode as taught in the prior art. Additionally, the practitioner will leave the probe (18) in one place before it is moved to deliver the appropriate amount of cold plasma (34) to treat the infected area for example, more than zero seconds but less than one minute. The practitioner may also return to one area and apply additional cold plasma (34) before concluding the treatment visit. The application of cold plasma inactivates or destroys the plurality of microbes and/or biofilm (32), including such common microorganisms, bacteria, and viruses which are leading to the infection and secondary symptoms, such as swelling. Thus, instead of requiring a surgical procedure, or administering an antibiotic, a treatment plan may be to administer the cold plasma once, twice, three or more times. For example, a treatment protocol may be one, two, three to five, or more times over the course of a 3-10-day period to effectively treat the symptoms, or in some cases, a single application may be sufficient for a given patient. While the treatment described in relation to FIG. 6 shows one particular style and shape of probe (18), it should be understood that the treatment can be administered using any of the various probes described herein.

TREATMENTS WITHIN THE MOUTH AND ESOPHAGUS: Barrett's esophagus is a condition in which the lining of the esophagus, the tube that connects the mouth to the stomach, is damaged by stomach acid. This damage causes the normal tissue lining the esophagus to be replaced by tissue that is similar to the lining of the intestine. Barrett's esophagus is often associated with long-term gastroesophageal reflux disease (GERD), a condition in which stomach acid frequently flows back into the esophagus, causing irritation and inflammation. It is considered a precancerous condition because people with Barrett's esophagus are at an increased risk of developing esophageal cancer. In some cases, endoscopic treatments may be recommended to remove abnormal tissue or to treat precancerous changes in the esophagus. Techniques such as radiofrequency ablation (RFA) or endoscopic mucosal resection (EMR) can be used to destroy or remove abnormal cells. Applicant has identified, however, that application of cold plasma can destroy abnormal cells. An advantage is that cold plasma also induces healing which other modalities do not, because the cold plasma generates immune healing responses at the target tissues. Thus, a practitioner can take a sample with a balloon while simultaneously or subsequently providing treatment of cold plasma to the tissue sample area.

TREATMENT OF TONSIL STONES: Tonsil stones, also known as tonsilloliths, are small, calcified deposits that form in the crevices of the tonsils, which are located at the back of the throat. These deposits are composed of microorganisms, dead cells, and debris that accumulate over time. Tonsil stones can range in size from tiny specks to larger, visible masses, and they can cause symptoms such as bad breath, sore throat, difficulty swallowing, and a persistent feeling of something stuck in the throat.

Treatment for tonsil stones depends on the severity of symptoms and the frequency of occurrence. There is not one good solution to treating tonsil stones. There are a myriad of social issues including causing bad breath, halitosis, as well as discomfort. Inadequate, nonmedical alternative treatments include: (i) gargling with salt water or nonalcoholic mouthwash to help reduce microorganisms and alleviate symptoms; (ii) using a water flosser or oral irrigator to gently rinse the tonsils and dislodge any visible tonsil stones; (iii) regularly brushing the teeth and tongue to remove microorganisms and food particles that contribute to tonsil stone formation; and/or (iv) throat lozenges or oral sprays may provide temporary relief from discomfort or bad breath.

The next minimally evasive solution is manual removal. For larger tonsil stones or persistent symptoms, a healthcare provider may manually remove the stones using a cotton swab or a specialized tool during an office visit. This procedure is called tonsil stone extraction or tonsil stone removal. The next level of treatment is antibiotics. If tonsil stones are associated with an underlying bacterial infection or other microorganisms or recurrent tonsillitis, a course of antibiotics may be prescribed to reduce inflammation and prevent further stone formation. However, antibiotics are typically not a long-term solution for tonsil stones. Finally, as a last resort, surgical intervention may be necessary. In cases of severe or recurrent tonsil stones that do not respond to other treatments, surgical removal of the tonsils (tonsillectomy) may be recommended. Tonsillectomy is usually considered a last resort due to the risks and potential complications associated with surgery, but it can provide permanent relief from tonsil stones in some cases.

As detailed herein, treatment of the tonsil, and of tonsil stones includes placing the probes of the current disclosure adjacent to the tonsils and applying cold plasma. In certain instances, removal of a tonsil stone can be performed first and then the cold plasma applied to provide antimicrobial treatment to the area, to reduce inflammation and the microbes causing the tonsil stones.

Medical conditions that originate in the nasal cavity can also be treated using the device (1) due to its small size and ability to be inserted into such small passages. Not only is cold plasma (34) effective in the removal of biofilm in the nasal cavity, it also is effective at reducing the size of tissue. Some of the conditions that can be treated with cold plasma (34) include but are not limited to: chronic, allergic, and vasomotor rhinitis, and alleviating sinus issues such as acute and chronic sinusitis. Allergic and vasomotor rhinitis can be treated by utilizing cold plasma (34) from the device (1) to selectively injure the posterior nasal nerves. Cold plasma (34) can also be utilized to reduce inferior turbinates and enlarged nasal swell bodies. Additionally, conditions of the ear, such as ceruminosis, can be treated with similar techniques by injuring the cerumen gland and peripheral nerves.

REDUCTION OF NASAL TURBINATES AND SWELL BODIES: Inferior turbinate hypertrophy refers to the enlargement or swelling of the inferior turbinates, which are structures located inside the nasal cavity. The inferior turbinates are responsible for warming, humidifying, and filtering the air we breathe. However, when they become hypertrophied, they can obstruct the nasal passage and lead to symptoms such as nasal congestion, difficulty breathing through the nose, snoring, and sleep disturbances. Treatment options for inferior turbinate hypertrophy depend on the severity of symptoms and may include starting with medications such as: (i) nasal corticosteroid sprays which can help reduce inflammation and swelling of the inferior turbinates, relieving nasal congestion and improving airflow; (ii) oral or topical decongestants which can temporarily shrink the blood vessels in the nasal lining, reducing swelling and congestion, however, they should be used cautiously and for short durations to avoid rebound congestion; and/or (iii) antihistamines for when allergies contribute to the hypertrophy, to help reduce allergic reactions and alleviate symptoms. An alternative to medications includes nasal irrigation such as saline nasal irrigation using a neti pot or squeeze bottle which can help clear mucus and reduce nasal congestion by flushing out irritants and allergens from the nasal passages. More evasive treatments include: (i) various in-office procedures, such as radiofrequency ablation, laser therapy, or submucosal resection, that can be performed to shrink or remove a portion of the hypertrophied inferior turbinates with the aim of reducing nasal obstruction and improving airflow without the need for surgery; and (ii) turbinate surgery (turbinoplasty or turbinectomy) for cases where conservative treatments are ineffective and symptoms are severe, surgical intervention may be considered to permanently reduce the size of the inferior turbinates which can involve removing a portion of the turbinate tissue or reshaping the turbinates to improve nasal airflow. Surgery is typically reserved for cases of refractory or severe nasal obstruction.

The cold plasma treatment described herein can be comfortably applied to the turbinate with minimal discomfort to reduce the size of the turbinate and improve nasal obstruction thus obviating the need for the aforementioned treatments.

TREATMENT OF MICROORGANISMS/VIRAL/BACTERIAL INFECTIONS IN NASAL CAVITIES: Sinusitis accounts for at least 20% of all antibiotic prescriptions and affects about 1 in 8 adults in the United States. The direct cost of managing acute and chronic sinusitis conservatively exceeds $11 billion per year. The indirect costs with lost days off work and school are heartbreaking. We estimate that 6% to 12% of patients in the Western world have chronic sinusitis. In addition, you must distinguish between acute from chronic sinusitis. As well as chronic sinusitis with or without nasal polyps because the treatments differ. Acute sinus infections clear up after a week or so and definitely do not last more than four weeks. On the other hand, the symptoms of a chronic sinus infection last for much longer, for at least 12 weeks. Unfortunately, there is not a medication approved for the majority of patients with chronic sinusitis to date. The only medications approved for chronic sinusitis are for those with nasal polyps. Nasal polyps account for 20% of those that suffer from chronic sinusitis. Nearly 50% of patients fail medical management and thus many are referred to ENTs for surgery. Many patients choose to avoid surgery and live with chronic sinusitis due to the risks of complications. Applying cold plasma directly treats biofilms, and pathogens in the sinus and nasal cavity. Applied using a wand, through catheter or sinus balloon the cold plasma can reach difficult areas in the nasal and sinus cavities as well as the eustachian tube.

Similarly, the nasal septal swell body (NSB) is a distinct structure located in the anterior part of the nasal septum (NS), adjacent to the anterior part of the middle turbinate and superior part of the inferior turbinate. It is very similar to the inferior turbinate and can cause nasal obstruction. Cold plasma can be used to decrease the size of the NSB and improve nasal breathing.

POSTERIOR NERVE ABLATION: Vasomotor rhinitis is a condition characterized by nasal congestion, sneezing, runny nose, or postnasal drip that occurs without any apparent allergic or infectious cause. It is sometimes referred to as nonallergic rhinitis because it is not caused by allergies. Instead, vasomotor rhinitis is believed to be triggered by environmental factors such as changes in temperature, humidity, air pollution, strong odors, or certain chemicals. The exact cause of vasomotor rhinitis is not fully understood, but it is thought to involve abnormal regulation of blood flow and nerve sensitivity in the nasal passages. Factors that may contribute to or exacerbate vasomotor rhinitis include: (i) temperature changes namely exposure to hot or cold air can trigger symptoms; (ii) humidity changes such as dry air or high humidity can irritate the nasal passages; (iii) strong odors such as perfumes, smoke, or chemical fumes may provoke symptoms; (iv) air pollution such as pollutants in the air, such as smoke or exhaust fumes, can irritate the nasal passages; (v) certain foods or drinks such as spicy foods, alcohol, or hot beverages may trigger symptoms in some individuals; and/or (vi) hormonal changes such as fluctuations in hormone levels, such as those that occur during pregnancy or menstruation, may affect nasal congestion. Treatment for vasomotor rhinitis typically involves avoiding triggers when possible and using medications to alleviate symptoms. Nasal corticosteroid sprays, antihistamines, decongestants, and nasal saline irrigation are commonly used to relieve congestion and other symptoms. There are several modalities to treat the posterior nasal nerve including RF and cryoablation. These treatments are inadequate. By contrast, treating these areas with the cold plasma treatments described herein is a safer option and causes less discomfort to the targeted areas which is a significant improvement over the prior art.

The figures and descriptions in this application depict specific examples to teach those skilled in the art how to make and use the best mode of the invention. These examples are not given to limit the scope of the invention but rather to teach inventive principles. To concisely teach inventive principles, some conventional aspects of the invention have been simplified or omitted. Those skilled in the art will appreciate many of the configurations, combinations, subcombinations, and variations on these examples that fall within the scope of the invention. For example, certain features of the invention described in separate embodiments can also be implemented in combination in a single embodiment. Conversely, various features that are described in the context of a single embodiment can also be implemented in multiple embodiments, separately or in any suitable subcombination. The invention is not limited to the specific illustrative examples described herein but by all embodiments and methods within the scope and spirit of the invention as in the current, amended, or added claims and their equivalents. In any case, all substantially equivalent systems, articles, and methods should be considered within the scope of the invention.

EXAMPLES

Example 1: Testing of Kill Rates

SAMPLE: 1 mL of overnight grown *E. coli* O157:H7 on LB ($2\times10^7$ cfu/mL) are spread on an LB agar petri dish and air dried at room temperature for thirty minutes. Inoculated plates are exposed to plasma for one, five, ten, and fifteen seconds with the different gas combinations. The plates are incubated at about 37° C. overnight and the microbial growth, and the absence of growth in the treatment regions are measured. The results of those measurements, the size of the inactivation circle, are then displayed in FIG. 2.

Several different gases were tested, each on a separate sample. The gases included ambient air at room temperature at 3 standard liters per minute (SLPM), $N_2$ gas at 3 SLPM, $N_2$ combined with NO (5,000 ppm) at 0.05 or 0.10 SLPM. Suction for each test was provided at 3 SLPM. In each case, the flow rate may be from 0.1 SLPM to 10 SLPM flow rate. Furthermore, the concentration of the NO, when combined with the $N_2$ gas, may be at a greater or lesser concentration than 5,000 ppm and added to reach a desired concentration within the range detailed herein. The probe in each case was placed at a distance of one millimeter from the surface of the plate. A charge for a given duration, specifically one, five, ten, and fifteen seconds, was applied and the side of the reduction of the *E. coli* was measured.

The study was then repeated, adding in different concentrations of NO gas, including concentrations of 0.01 and 0.15 in addition to the aforementioned 0.05 and 0.10 of the prior test. The study tested *Streptococcus pyogenes* inactivation in the same manner as the prior test for *E. coli*.

Example 2: Testing of Temperature

A sample setup similar to that of FIG. 1B was provided, but instead of bacteria and agar, the cold plasma was applied to a small metal plate placed one millimeter from the cold plasma and holding the device for up to ten minutes to determine the differences in temperature among the various gas mixtures being utilized.

Example 3: Testing of Ozone Concentration

Ozone concentration was tested by creating cold plasma for a time duration, and then using an ozone monitor to test for the presence and concentration of ozone for the duration of the test.

Applicant therefore has created a new and useful device, including plasma probes that provide for therapeutic treatment by application of cold (nonthermal) plasma. The devices, together with a flow of gas and a suction line, create highly charged particles that serve as a broad spectrum antimicrobial yet dissipate into nontoxic materials shortly after their creation. Furthermore, based on the flow of gasses, plasma is created more broadly than applications that do not use the flow of gas, and such gasses further generate sufficient particles to not only meet, but exceed the killing power of nonthermal plasma created in ambient air alone. Finally, the use of such gases dramatically reduces the production of ozone, leading to therapeutic opportunities for treatment as detailed herein.

What is claimed is:

1. A cold plasma device comprising:
   a probe, said probe comprising a conductor wire extending from a proximal end to a distal end and having a tip at said distal end;
   wherein the conductor wire comprises an insulating material along a length of the probe from the proximal end to the distal end with a portion of noninsulated material at each end of the conductor wire and wherein the tip comprises a conductive gallium alloy, said gallium alloy having a melting point of about 40° C.;
   a first passage having a first opening adjacent to the tip and a second passage having a second opening adjacent to the tip, said first passage being a gas delivery line and said second passage being a suction line, said first passage and said second passage disposed on opposing sides of the probe with the probe positioned centrally and in line between the first passage and the second passage;
   wherein the first opening and the second opening each are dimensioned to be noncircular, having a first dimension along a width and a second dimension along a length; and
   a power source generating 10,000-45,000 V at a pulse of 0.1 μs to 1 s in duration applied at 100 Hz to 10,000 Hz.

2. The cold plasma device of claim 1 wherein the power source generates 17,000-37,000 V pulses of 1-5 us in duration applied at 1,000 Hz.

3. The cold plasma device of claim 1 wherein the probe is connected to a pressurized gas and a wiring harness, said wiring harness connected to a power source.

4. The cold plasma device of claim 1 wherein the conductor wire is surrounded by an epoxy along a length of the probe from the proximal end to the distal end.

5. The cold plasma device of claim 1 wherein the first passage and the second passage are attached to the probe by a means selected from the group consisting of: an outside portion of the probe, a recess within the probe, being comprised within the probe, and combinations thereof.

6. The cold plasma device of claim 1 wherein the first passage is provided with nitrogen gas.

7. The cold plasma device of claim 1 wherein the first passage is provided with a mixture of nitrogen gas and nitric oxide.

8. The cold plasma device of claim 7 wherein the first passage is provided with a mixture of nitrogen gas and nitric oxide at a concentration of the nitric oxide of 5,000 ppm and a flow rate of between 0.01 standard liters per minute (SLPM) and 0.15 SLPM.

9. The cold plasma device of claim 1 comprising:
   a suction of between 0.1 SLPM and 10 SLPM of flow within the second passage; and
   a flow of a combination of nitrogen gas and nitric oxide, said nitric oxide at between 1,000 ppm and 10,000 ppm, having a standard liter per minute flow of 0.01 SLPM to 0.15 SLPM.

10. A method of treatment of tonsillitis comprising administering to a patient in need thereof an effective amount of cold plasma, said cold plasma administered by applying a quantity of cold plasma from a probe from a cold plasma device of claim 1.

11. The method of treatment of claim 10 wherein the cold plasma is administered by providing a flow of nitrogen gas to a tip of the probe.

12. The method of treatment of claim 10 wherein the cold plasma is generated from a probe, said probe comprising:
   a conductor wire extending from a proximal end to a distal end and having a tip at said distal end;
   a first passage having a first opening adjacent to the tip and a second passage having a second opening adjacent to the tip; and
   a power source generating 10,000-45,000 V at a pulse of 0.1 us to 1 s in duration applied at 100 Hz to 10,000 Hz.

13. The method of treatment of claim 12 wherein the conductor wire comprises an insulating material along a length of the probe from the proximal end to the distal end with a portion of noninsulated material at each end of the conductor wire.

14. The method of treatment of claim 13 wherein the probe is connected to a pressurized gas selected from the group consisting of: $N_2$ gas or $N_2$ gas mixed with nitric oxide; wherein said pressurized gas is configured to flow into the first passage; wherein the probe is connected a wiring harness, said wiring harness connected to a power source; and wherein the probe is defined to provide suction from the second opening adjacent to the tip and through the second passage.

* * * * *